(12) United States Patent
D'Andrade

(10) Patent No.: US 9,791,246 B2
(45) Date of Patent: Oct. 17, 2017

(54) STIMULANT TARGET UNIT AND ACCESSORY FOR A STIMULANT TARGET UNIT

(71) Applicant: FITLIGHT SPORTS CORP., Aurora (CA)

(72) Inventor: Derek D'Andrade, King (CA)

(73) Assignee: FITLIGHT SPORTS CORP., Aurora, Ontario ( * ) Notice: Subject to any disclaimer, the term of this patent is extended or adjusted under 35 U.S.C. 154(b) by 0 days.

(21) Appl. No.: 14/839,523

(22) Filed: Aug. 28, 2015

(65) Prior Publication Data

US 2017/0059286 A1   Mar. 2, 2017

(51) Int. Cl.
*A63B 69/00* (2006.01)
*F41J 5/04* (2006.01)
(Continued)

(52) U.S. Cl.
CPC ............ *F41J 5/14* (2013.01); *A63B 24/0021* (2013.01); *A63B 24/0087* (2013.01);
(Continued)

(58) Field of Classification Search
CPC .................. A63B 63/00; A63B 63/04; A63B 2024/004–2024/005; A63B 69/0026; F41J 5/04; F41J 5/052; F41J 5/056; F41J 5/06
(Continued)

(56) References Cited

U.S. PATENT DOCUMENTS 3,972,531 A * 8/1976 Knapp ........................ F41J 5/04
273/376
4,216,968 A * 8/1980 Yeeda ........................ F41J 5/04
200/5 A
(Continued)

FOREIGN PATENT DOCUMENTS

CA   1203258 A1   4/1986
CA   2165923 A1   6/1997
(Continued)

OTHER PUBLICATIONS

Ludvigsen, et al., "TacTowers: An Interactive Training Equipment for Elite Athletes", DIS 2010, Aug. 16, 2010, pp. 112-415, Aarhus, Denmark.
(Continued)

*Primary Examiner* — Mark Graham
(74) *Attorney, Agent, or Firm* — Millman IP, Inc.

(57) ABSTRACT

A stimulant target unit including: a housing, at least one stimulation source configured to provide a stimulus to stimulate a user, a contact sensor configured to detect an impact to the stimulant target unit and triggered by an impact that is within a selected range of impact forces, a feedback system configured to inform the user the stimulant target unit has been actuated in response to the stimulus, a controller programmed to register triggering of the contact sensor, a protective cover configured to retain the stimulant target unit and a mounting structure configured to connect the stimulant target unit to a support structure. The mounting structure
(Continued)

includes a vibration isolator configured to, over the selected range of impact forces, inhibit transmission of force from an impact within the selected range of impact forces on the support structure to the contact sensor sufficiently to prevent the triggering of the contact sensor.

8 Claims, 25 Drawing Sheets

(51) Int. Cl.
　　　*F41J 5/14*　　　(2006.01)
　　　*A63B 63/00*　　(2006.01)
　　　*A63B 71/06*　　(2006.01)
　　　*A63B 24/00*　　(2006.01)
　　　*F41J 1/10*　　　(2006.01)
　　　*F41J 5/056*　　(2006.01)
　　　*F41J 1/01*　　　(2006.01)
　　　*A61B 5/16*　　　(2006.01)

(52) U.S. Cl.
　　　CPC ........ *A63B 63/004* (2013.01); *A63B 69/0024* (2013.01); *A63B 69/0026* (2013.01); *A63B 69/0053* (2013.01); *A63B 71/0622* (2013.01); *F41J 1/01* (2013.01); *F41J 1/10* (2013.01); *F41J 5/056* (2013.01); *A61B 5/162* (2013.01); *A63B 2024/004* (2013.01); *A63B 2071/063* (2013.01); *A63B 2071/0625* (2013.01); *A63B 2207/02* (2013.01); *A63B 2220/40* (2013.01); *A63B 2220/53* (2013.01); *A63B 2220/801* (2013.01); *A63B 2225/50* (2013.01); *A63B 2225/54* (2013.01)

(58) Field of Classification Search
　　　USPC ......... 473/446; 273/371, 372, 374, 375, 376
　　　See application file for complete search history.

(56) References Cited

U.S. PATENT DOCUMENTS

| | | | |
|---|---|---|---|
| 4,245,843 A * | 1/1981 | Griggs | A63B 63/00 273/380 |
| 4,333,657 A * | 6/1982 | Jaworski | F41J 5/04 273/368 |
| 4,561,660 A * | 12/1985 | Zammuto | F41J 3/0042 273/376 |
| 4,607,842 A * | 8/1986 | Daoust | A63B 24/0021 124/51.1 |
| 5,029,873 A * | 7/1991 | Davis | F41J 5/056 273/376 |
| 5,370,386 A * | 12/1994 | Parks | A63B 63/00 273/400 |
| 5,634,640 A | 6/1997 | McCarrel | |
| 5,812,239 A | 9/1998 | Eger | |
| 5,888,153 A | 3/1999 | Masin | |
| 6,093,160 A | 7/2000 | Augustine | |
| 6,402,641 B1 * | 6/2002 | Lee | A63B 63/00 273/127 R |
| 6,551,205 B1 * | 4/2003 | Koelzer, Jr. | A63B 63/00 473/454 |
| 6,554,284 B2 * | 4/2003 | Chou | A63B 63/00 273/371 |
| 7,192,387 B2 | 3/2007 | Mendel | |
| 7,981,009 B2 | 7/2011 | Brenner et al. | |
| 7,999,694 B2 * | 8/2011 | Martin | F41J 5/02 340/323 R |
| 8,002,283 B1 * | 8/2011 | Jones | A63B 63/00 273/343 |
| 8,052,545 B1 * | 11/2011 | Assenheimer, III | A63B 63/003 473/422 |
| 8,109,845 B2 * | 2/2012 | Duty | A63B 24/0021 273/381 |
| 8,376,852 B2 * | 2/2013 | Kao | A63F 9/24 273/371 |
| 8,777,818 B1 | 7/2014 | Tate, Jr. | |
| 2002/0042312 A1 * | 4/2002 | Decloux | A63B 63/004 473/476 |
| 2002/0103024 A1 | 8/2002 | Jeffway, Jr. | |
| 2002/0117804 A1 * | 8/2002 | Chou | F41J 5/044 273/371 |
| 2003/0085870 A1 | 5/2003 | Hinckley | |
| 2003/0199342 A1 | 10/2003 | Birss | |
| 2005/0065452 A1 | 3/2005 | Thompson | |
| 2005/0167907 A1 | 8/2005 | Curkendall et al. | |
| 2006/0089213 A1 | 4/2006 | Snyder | |
| 2007/0176368 A1 * | 8/2007 | Lamberti | A63B 69/0097 273/371 |
| 2007/0184920 A1 * | 8/2007 | Mah | A63B 69/0026 473/446 |
| 2007/0191141 A1 | 8/2007 | Weber | |
| 2008/0125288 A1 | 5/2008 | Case | |
| 2008/0176665 A1 | 7/2008 | Snyders | |
| 2008/0261727 A1 | 10/2008 | Snyder | |
| 2009/0264262 A1 | 10/2009 | Brenner et al. | |
| 2010/0296285 A1 | 11/2010 | Chemel | |
| 2010/0324443 A1 | 12/2010 | Ashton-Miller et al. | |
| 2015/0273296 A1 * | 10/2015 | Marcin | A63B 63/003 473/446 |
| 2016/0107057 A1 * | 4/2016 | Wisegarver | A63B 71/0605 473/446 |

FOREIGN PATENT DOCUMENTS

| | | |
|---|---|---|
| CA | 2536020 A1 | 8/2007 |
| EP | 0403130 A1 | 12/1990 |
| GB | 2270004 A | 3/1994 |
| JP | 11253502 A | 9/1999 |
| JP | 2010253236 A | 11/2010 |
| WO | 2005/049154 A2 | 6/2005 |
| WO | 2006/053000 A2 | 5/2006 |
| WO | 2007/060401 A1 | 5/2007 |
| WO | 2007/142588 A1 | 12/2007 |
| WO | 2013/071408 A1 | 5/2013 |

OTHER PUBLICATIONS

PCT/CA2012/001048, International Search Report, Feb. 7, 2013.
Bech, Rasmus, "Erik Roads have been to mastermind: 'Best invention since the ball'", Politiken Newspaper, Dec. 2, 2013, Politiken.dk.
EP12849537.1, Communication pursuant to Rule 114(2) EPC, Aug. 12, 2014.
EP12849537, European Search Report, May 21, 2015.
Fitlight Webpage Inventor Bio, http://www.fitlighttraining.com/fliight.aspx, date unknown, FitLight.
"Erik Roads have invented new training system", http://www.opfind.nu, date unknown.
EP15187969.9, Extended European Search Report, Jun. 20, 2016.
Office Action dated Feb. 19, 2016 in connection with U.S. Appl. No. 14/356,448.
Office Action dated Feb. 24, 2017 in connection with U.S. Appl. No. 14/356,448.

* cited by examiner

STIMULANT TARGET UNIT AND ACCESSORY FOR A STIMULANT TARGET UNIT

FIELD

The specification relates generally to systems for exercising human reaction to stimuli and more particularly to a stimulant target unit and an accessory for a stimulant target unit.

BACKGROUND OF THE DISCLOSURE

Target training can increase accuracy for those involved in sports, such as hockey, and also tactical activities. For example, in tactical training, a target is set at a distance from the user and the user fires a projectile at the target, such as a non-lethal round of ammunition. The user is able to measure their accuracy based on holes left, (if any), by the round of ammunition on the target. Having to physically inspect the target each time the user fires the projectile can be quite cumbersome.

Some devices have been proposed, which have impact sensors built in, which can therefore record an impact. However, such devices are typically incapable of withstanding high-energy impacts associated with such things as rounds of ammunition or hockey pucks.

It would be advantageous to provide a device that could withstand such high-energy impacts in order to permit its use when training athletes such as hockey players and users of firearms.

SUMMARY OF THE DISCLOSURE

According to a non-limiting embodiment, there is provided an accessory for a stimulant target unit. The stimulant target unit includes a contact sensor, a primary contact member that is contactable to trigger the contact sensor over a first range of impact forces, and a controller programmed to receive signals indicative of triggering of the contact sensor. The accessory includes a protective cover configured to cover the primary contact member and to be spaced by a selected spacing from the contact member. The spacing is selected to permit the cover member to receive an impact and transmit the impact to the primary contact member to trigger the contact sensor over a second range of impact forces that is higher than the first range of impact forces.

Optionally, the accessory further includes a mounting structure configured to connect the stimulant target unit to a support structure.

Optionally, the mounting structure includes a vibration isolator configured such that, the contact sensor is configured to be triggered by an impact that is within a selected range of impact forces, and wherein the vibration isolator inhibits transmission of force from an impact within the first selected range of impact forces on the support structure to the contact sensor sufficiently to prevent the triggering of the contact sensor.

According to another non-limiting embodiment, there is provided a stimulant target unit that includes a housing, at least one stimulation source coupled to the housing, the stimulation source configured to provide a stimulus to stimulate a user, a contact sensor coupled to the housing and configured to detect an impact to the stimulant target unit, a feedback system configured to inform the user that the stimulant target unit has been actuated in response to the stimulus, a controller programmed to register triggering of the contact sensor, a protective cover configured to retain the stimulant target unit and a mounting structure configured to connect the stimulant target unit to a support structure. The mounting structure includes a vibration isolator configured such that, the contact sensor is configured to be triggered by an impact that is within a selected range of impact forces, and wherein the vibration isolator inhibits transmission of force from an impact within the selected range of impact force on the support structure to the contact sensor sufficiently to prevent the triggering of the contact sensor.

BRIEF DESCRIPTIONS OF THE DRAWINGS

For a better understanding of the various embodiments described herein and to show more clearly how they may be carried into effect, reference will now be made, by way of example only, to the accompanying drawings in which.

DETAILED DESCRIPTION

Figure 1:
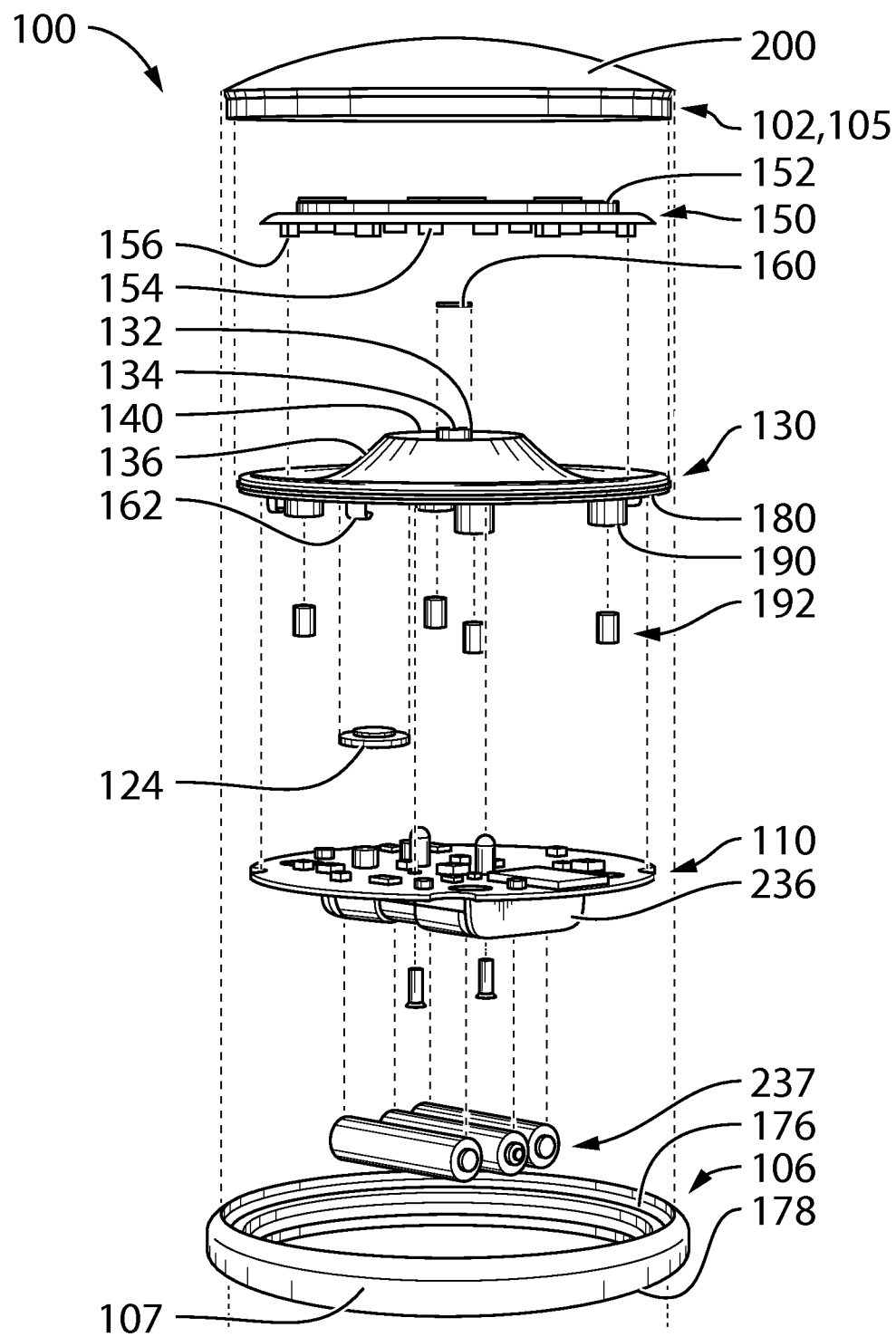
FIG. 1 is an exploded view of a stimulant target unit showing a first set of components, according to a non-limiting embodiment.

Described herein are stimulant target units (examples of which are shown at 100 in exploded views in FIGS. 1 and 2) and accessories for stimulant target units. Each stimulant target unit includes a contact sensor (an example of which is identified at 370 in FIG. 7), a primary contact member, (an example of which is shown at 102 in FIG. 1), which is contactable to trigger the contact sensor over a first range of impact forces, (including, for example, a force of a person hitting the primary contact member), and a controller, (an example of which is identified at 352 in FIG. 7), which is programmed to receive signals indicative of triggering of the contact sensor. Each accessory includes a protective cover, (an example of which is shown at 625 in FIGS. 12a-12c), which is configured to cover the primary contact member and to be spaced by a selected spacing from the contact member. The spacing is selected to permit the cover member to receive an impact and transmit the impact to the primary contact member to trigger the contact sensor over a second range of impact forces that is higher than the first range of impact forces (including, for example, the force from a hockey puck at 100 mph impacting the protective cover, or for example, the force from an impact by training ammunition fired from a firearm against the protective cover during a tactical training exercise).

Optionally each accessory further includes a mounting structure, (an example of which is shown at 610 in FIG. 11), which is configured to connect the stimulant target unit to a support structure. When the stimulant target unit is mounted to a support structure, it is desirable to inhibit an impact by a projectile (e.g. a puck or a round of ammunition) on the support structure from transmitting strong enough forces into the stimulant target unit to cause a "false" or incorrect registration of an impact on the stimulant target's protective cover. At least in some embodiments, the mounting structure includes a vibration isolator that is configured to inhibit the transmission of sufficient force from an impact to the supporting structure that is within the second selected range of impact forces to the contact sensor to prevent triggering the contact sensor in these scenarios.

According to a non-limiting embodiment, there is provided an accessory for a stimulant target unit. The stimulant target unit includes a contact sensor, a primary contact member that is contactable to trigger the contact sensor over a first range of impact forces, and a controller programmed to receive signals indicative of triggering of the contact sensor. The accessory includes a protective cover configured to cover the contact member and to be spaced by a selected spacing from the contact member, and a mounting structure configured to connect the stimulant target unit to a support structure. The spacing is selected to permit the cover member to receive an impact and transmit the impact to the primary contact member to trigger the contact sensor over a second range of impact forces that is higher than the first range of impact forces.

It is understood that for the purpose of this disclosure, language of "at least one of X, Y, and Z" and "one or more of X, Y and Z" can be construed as X only, Y only, Z only, or any combination of two or more items X, Y, and Z (e.g., XYZ, XYY, YZ, ZZ).

It is also understood that the terms "couple", "coupled", "connect", "connected" are not limited to direct mating between the described components, but also contemplate the use of intermediate components to achieve the connection or coupling.

Figure 2:
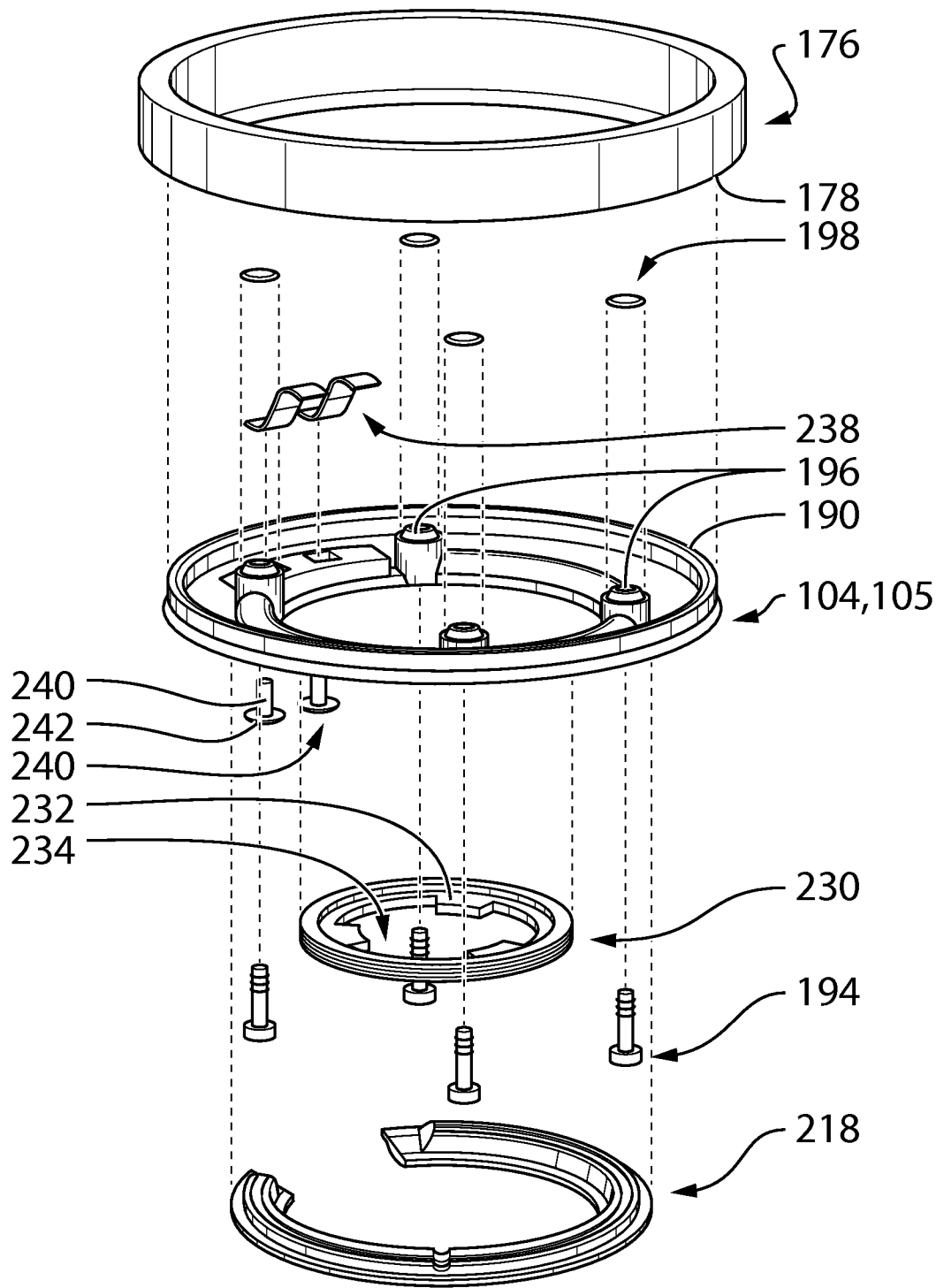
FIG. 2 is an exploded view the stimulant target unit of FIG. 1, showing a second set of components, according to a non-limiting embodiment.

FIGS. 1 and 2 depict an exploded view of an example stimulant target unit 100 (referred to individually as "stimulant target unit 100" and collectively as "stimulant target units 100"). The stimulant target unit 100 includes an upper shell 102 and a lower shell 104 that together form a housing 105. According to some embodiments, the upper shell 102 is transparent and the lower shell 104 is opaque. A rim 106 surrounds the upper and lower shells 102, 104 to join the two parts along their peripheries as discussed in greater detail below.

Figure 4:
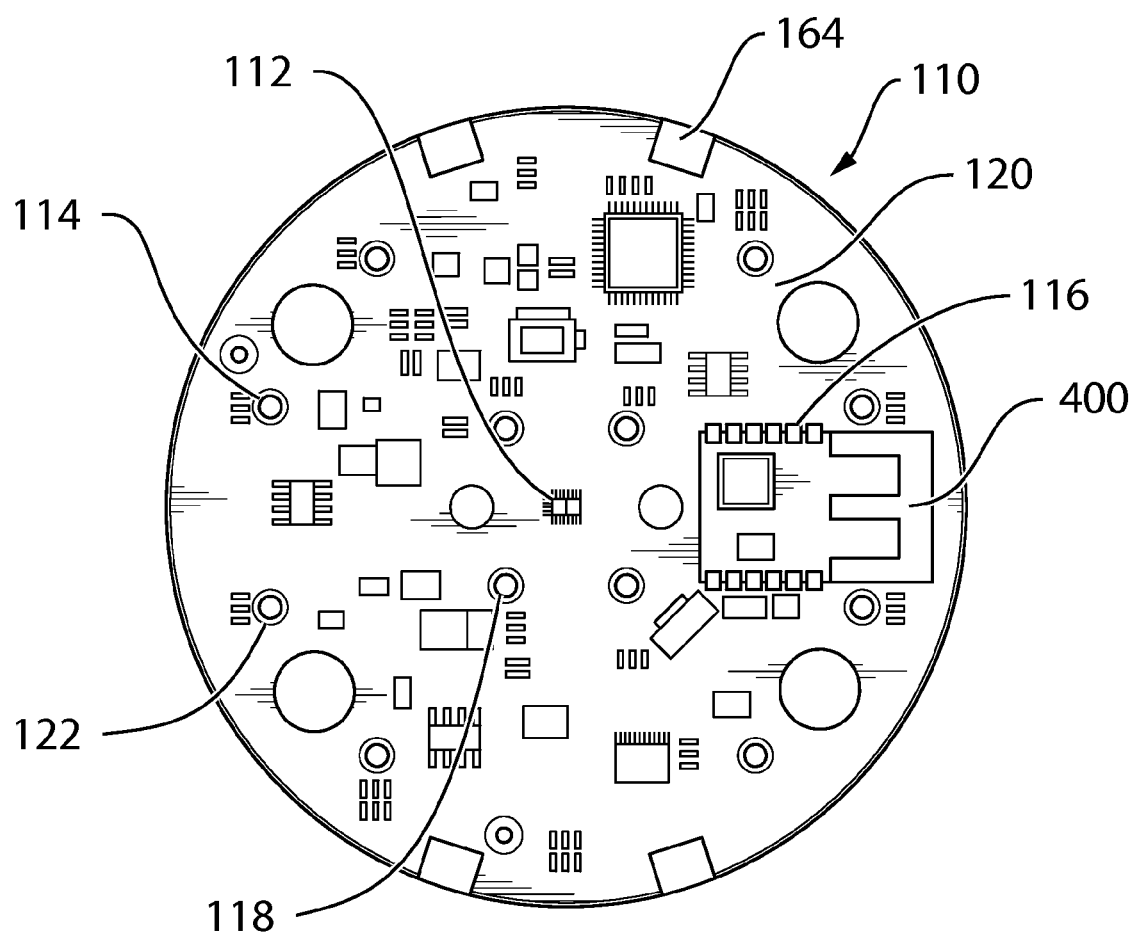
FIG. 4 is a top view of a printed circuit board of the stimulant target unit of FIG. 1, according to a non-limiting embodiment.

A printed circuit board ("PCB") 110 is disposed in the housing between the upper and lower shells 102, 104. The PCB 110 carries circuit components, mechanisms and/or systems for generating originating stimulus (e.g., lights, sound), measuring reaction or response time of the individual being trained, and generating feedback stimulus (e.g., lights, sound) for the trainee to confirm that he or she has adequately responded to the stimulus. In the illustrated embodiment the PCB 110 carries a centrally located infrared ("IR") receiver 112, a surrounding inner annulus 114 of IR emitters 116 and surface mounted light emitting diodes ("LEDs") 118, and an outer annulus 120 of surface mounted LEDs 122. The inner annulus 114 may, for example, include two IR emitters 116 located 180 degrees apart and four LEDs 118 (FIG. 4) positioned along the inner annulus 114 in an "X" arrangement. The outer annulus 120 may, for example, include ten equidistantly spaced LEDs 122. The LEDs 118, 122 can be multi-coloured light sources in which the colour output can be controlled, as known in the art. A speaker 124 may also be connected to the PCB 110.

Figure 3A:
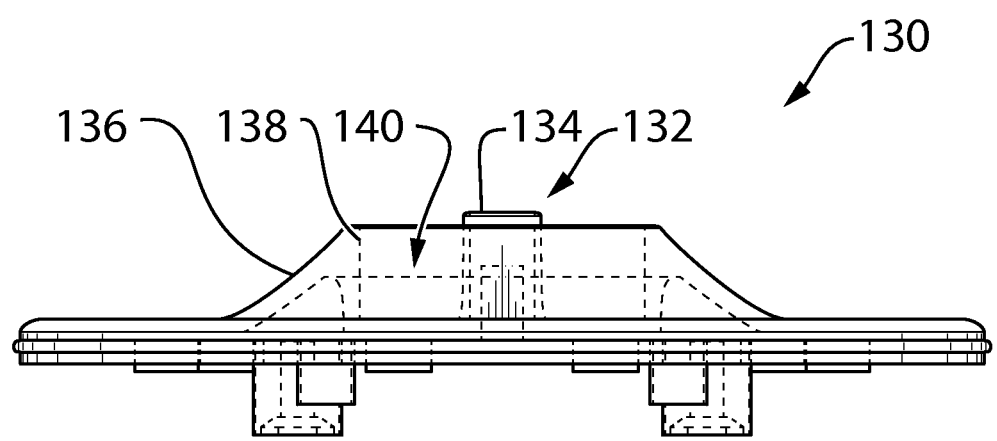
FIG. 3A is a side view of an inner cover of the stimulant target unit of FIG. 1, according to a non-limiting embodiment.
Figure 3B:
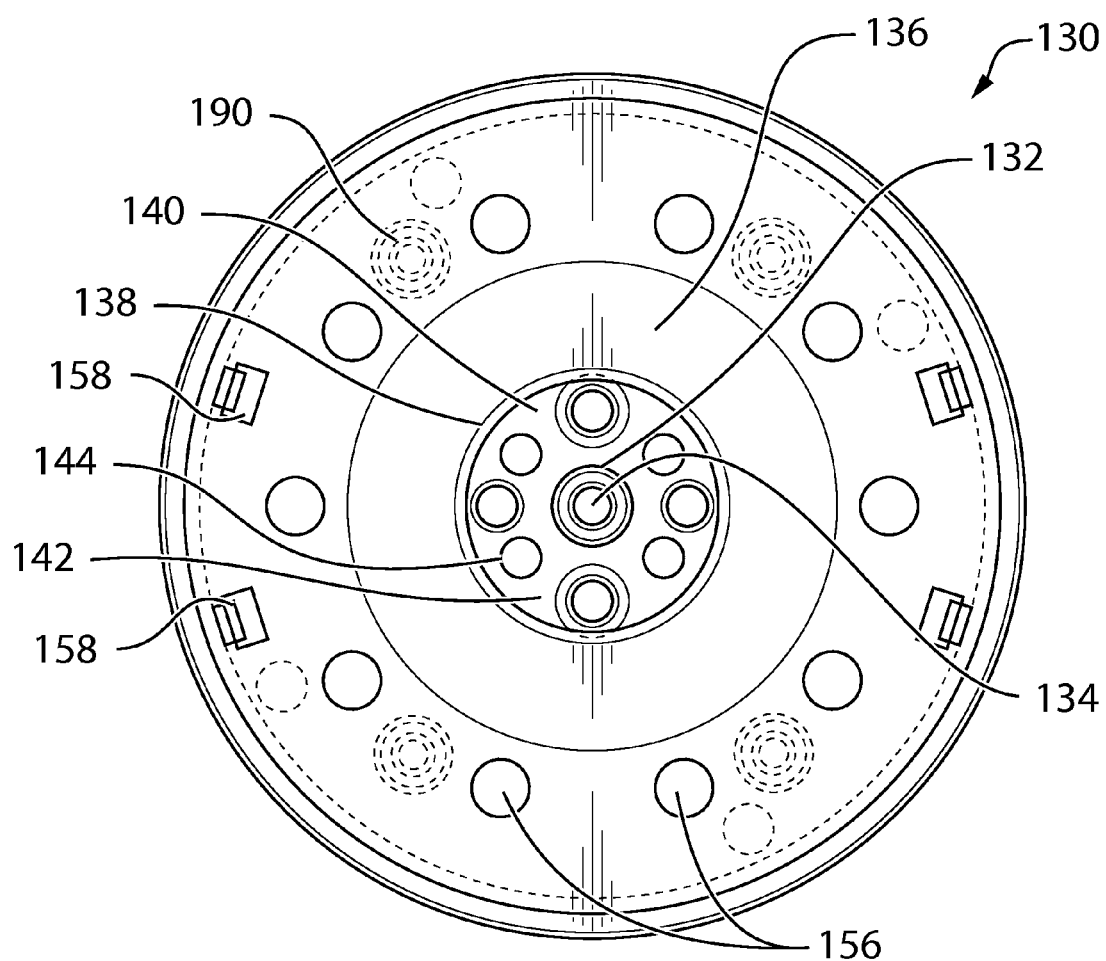
FIG. 3B is a top view of the inner cover shown in FIG. 3A, according to a non-limiting embodiment.

An opaque inner cover 130 is positioned over the PCB 110. As shown in FIGS. 3A and 3B, the inner cover 130 has a central tube 132 having a central aperture 134 that registers with the IR receiver 112. The central tube 132 is surrounded by a frusto-conical shield 136 that has an inboard axial annular wall 138 with an elevation that is nearly or substantially equal to that of the central tunnel tube 132. Collectively the central tube 132 and inboard axial annular wall 138 form a toroidal tube or tunnel 140 coaxial with the central tube 132. The co-axial tunnel 140 has a radial floor 142 with a series of holes 144 therein that register with the components (IR emitters 116 and LEDs 118) of the inner annulus 114. Outboard of the frusto-conical shield 136 the inner cover 130 features an annular series of holes 146 arranged to coincide with the positions of the outer annulus LEDs 122 so that the light from these LEDs shine through the inner cover 130.

An annular light pipe or guide 150 is mounted atop the inner cover 122. The light guide 150 has an integrally formed ring 152 with downwardly projecting light guiding digits 154 that pass through the inner cover holes 146 to contact the surface mount LEDs 122. The digits 154 guide light from the LEDs 122 to the ring 152, which in turns distributes the light generated by the LEDs 122 around the ring 152 to thereby provide a more uniform ring-shaped light pattern as opposed to a series of point sources. This may make the stimulant target unit 100 more visible under sunny or bright conditions.

The co-axial tunnel 140, which may have walls that absorb light (and may for example, have a roughened surface texture) helps to reduce the spread of IR light emanating from the IR emitters 116 and direct the IR light along a more focused beam. The central tube 132, which may also have walls that absorb light and may include an inward taper or inward jog, helps to insulate the IR receiver 116, which is located at the bottom of the central tube 132, from stray light. In addition, an O-ring 160 is mounted between the central tube 132 and the upper shell 102 in order to reduce or eliminate any IR light emanating out of the coaxial tunnel 140 from leaking into the central tube 132. Individually and collectively, these features aid in creating a more accurate emission path and reducing the deactivation field, thus requiring the user to be more accurate in actuating the stimulant target unit 100.

The stimulant target unit 100 can be constructed to withstand considerable forces and stresses. The components can be interconnected as follows:

The light guide 150 connects to the inner cover 130 by a number of resiliently deformable clips 156 integrally formed on the underside of the light guide 150 that snap into mounting holes 158 formed in the inner cover 130.

The PCB 110 connects to the inner cover 130 via a number of resiliently deformable clips 162 integrally formed on the underside of the inner cover 130 that snap into rebates 164 formed along the outer periphery of the PCB 110.

The inner cover 130, having the light guide 150 and the PCB 110 attached thereto, also connects to the upper shell 102 via a snap fit. As shown in the detailed assembly cross-section view FIG. 5, the inner cover 130 has an outer peripheral reinforcing flange 170 that is downwardly tapered on its top surface. The outer flange 170 joins a straight outer sidewall 172 with an integrally formed projecting snap ring 174. The upper shell 102 has an axially extending circumferential flange 180 with a complementary shape along the inner diameter thereof. The complementary shape includes an annular rebate 182 sized slightly smaller than the snap ring 174 so that the snap ring 174 locks (releasably) into the annular rebate 182 of the resiliently deformable axially extending circumferential flange 180.

Referring to FIGS. 1 and 2, the upper shell 102, having the inner cover 130, light guide 150 and PCB 110 attached thereto as previously described, is suspendingly connected to the lower shell 104 via the rim 106, which can be formed from an elastomeric material such as rubber. The rim 106 features an upper annular groove 176 and a lower annular groove 178. The upper shell 102 includes an axially extending circumferential flange 180 that sits in and runs along the rim of the upper annular groove 176. The lower shell 104 has an axially extending circumferential flange 190 that seats in and along the rim lower annular groove 178. The inner cover 130 has a series of mounting cavities 190 integrally formed on the underside thereof. Threaded socket inserts 192 are fixed (e.g., via thermal bonding) in the mounting cavities 190. (The mounting cavities 490 could alternatively be constructed with integrally formed threaded sockets.) Carriage bolts 194, each having a head 194*a*, a smooth shaft 194*b* proximate the head and a threaded shaft 194*c* distal the head, are passed through mounting bores 196 formed in the lower shell to fasten together the lower shell 104, rim 106, and inner cover 130/upper shell 102 assembly. (O-rings 198 may be disposed between the mounting bores 196 and the PCB 110.) This manner of connection enables the upper shell 102 and lower shell 104 to move axially relative to one another when, for example, the upper shell 102 is impacted and deforms the elastomeric rim 106.

Figure 5:
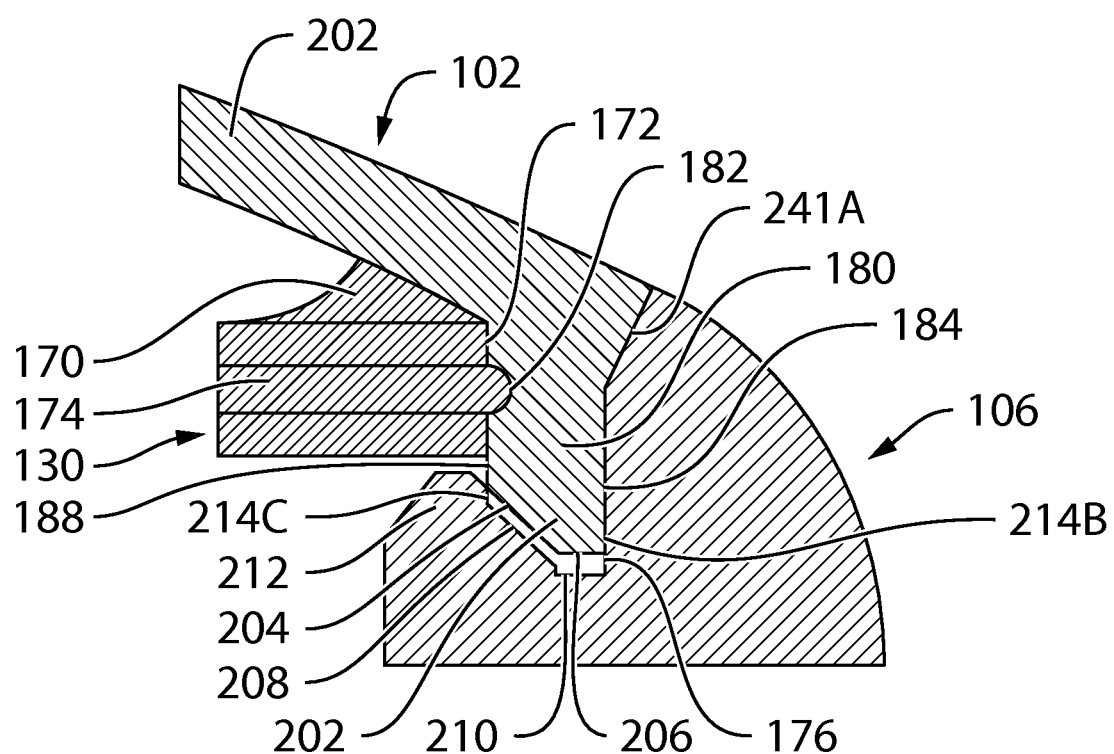
FIG. 5 is a detail cross-section of a portion of housing of the stimulant target unit of FIG. 1, according to a non-limiting embodiment.

FIG. 5 provides more detail on how impact forces are handled by the stimulant target unit 100.

The translucent upper shell 102 may be formed from an impact resistant polymer such as a polycarbonate. The upper shell 102 may be domed-shaped, having a semi-spherical top surface 200 (which is semi-circular in cross-section). The upper shell axially extending circumferential flange 180 has an outboard face 184 that is matched by an outboard wall 186 of the rim upper groove 176 and an inboard face 188 that is partially met by an inboard wall 189 of the rim upper groove 176. The upper shell axially extending circumferential flange 180 also has a bottom portion 202 with a canted wall 204 joining a flat end face 206, however, the bottom portion 202 does not fully seat into the complementarily shaped canted 208 and bottom walls 210 of the rim upper groove 176, i.e., there is normally a space between walls 204, 208 and 206, 210. The domed shape of the upper shell 102 helps to transfer impact forces to the outboard periphery thereof. The force will have an axial component and a transverse component. The transverse component of the force will be resisted by the outboard wall 186 of the rim 106. The axial component of the force drives the axially extending circumferential flange 180 downward to be resisted by the canted and bottom walls 208, 210 of the rim upper groove 176. In the process, the bottom portion 102 of the axially extending circumferential flange 180 could deflect or deform an inboard finger portion 212 of the rim 106.

The axially extending circumferential flange 190 of the lower shell 104 is similarly shaped and installed in the similarly shaped rim lower groove 178, which provides the lower shell 104 with room to move relative to the rim 106.

As shown in FIG. 5, the above described construction provides a three point seal at 214a, 214b and 214c between the upper (or lower) shell 102 and the rim 106, which is effective in enabling the stimulant target unit 100 to be water resistant and used under wet conditions such as in the rain or in swimming pools. The domed shape of the upper shell 102, having its most elevated region over the IR emitters and receivers 112, 116 also aids in directing water that would otherwise interfere with the sensors away from the sensors so that the stimulant target unit 100 can be used in wet conditions. Alternative embodiments may use other shapes instead of a dome to allow water to flow away from the IR sensor, such as pyramidal or conical.

Figure 6:
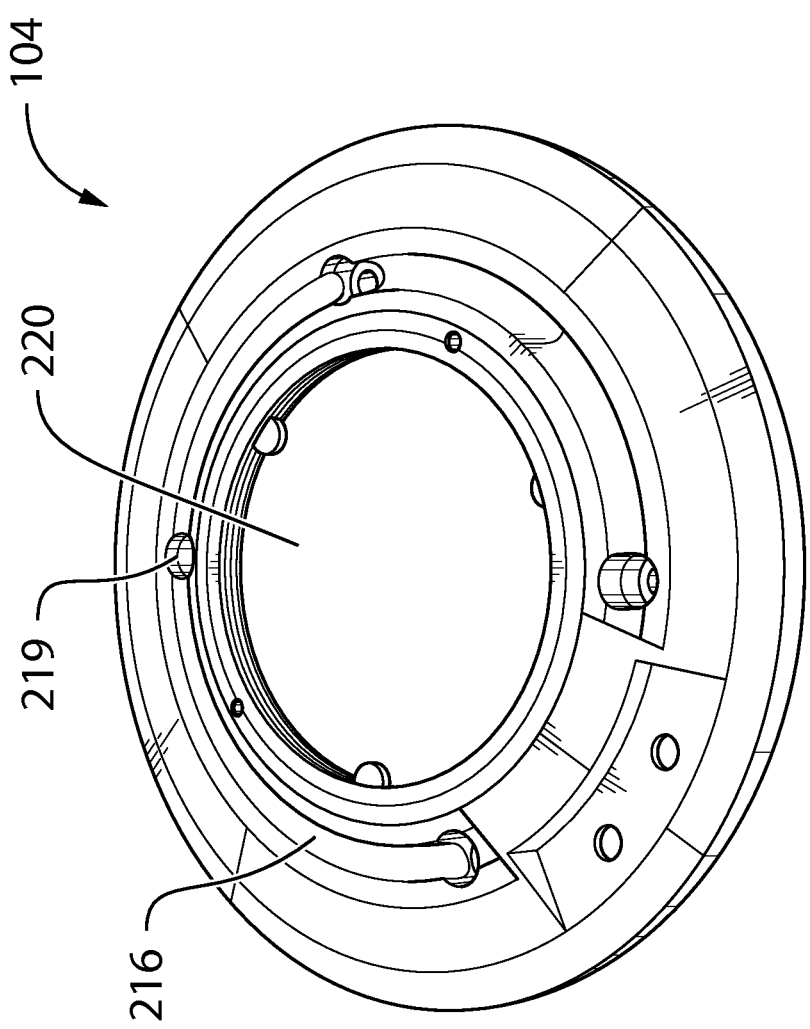
FIG. 6 is a bottom perspective view of a shell of the housing of the stimulant target unit shown in FIG. 1, according to a non-limiting embodiment.

Referring additionally to the bottom perspective view of the lower shell in FIG. 6, the lower shell 104 has a semi-circular groove 216 having holes 219 therealong through which the carriage bolts 194 are passed. The bolt heads 194a seat within the groove 216 so as not to be exposed. An elastomeric seal 218 (FIG. 2) is provided to cap this groove 216.

The lower shell includes a cavity 220 on an underside thereof to which a lock member 230 is mounted. The lock member 230 includes a plurality of radially oriented lugs 232 and intervening rebates 234 which are collectively intended to inter-engage with corresponding features of a mating lock member on a mounting structure, as described further below.

The underside of the PCB 110 has a battery compartment 236 mounted thereon for holding batteries 237. The batteries 237 may be replaceable and rechargeable batteries. The lower shell 104 has two leaf springs 238 mounted thereon that are disposed to contact relatively large electrically conductive pads (not shown) on the underside of the PCB 110 that are electrically connected to the batteries. The leaf springs 238 are riveted to the lower shell 104 by rivets 240 have electrically conductive heads 242 which provide external charging ports that can be used to recharge the batteries in the compartment 236 without having to remove the batteries.

Figure 7:
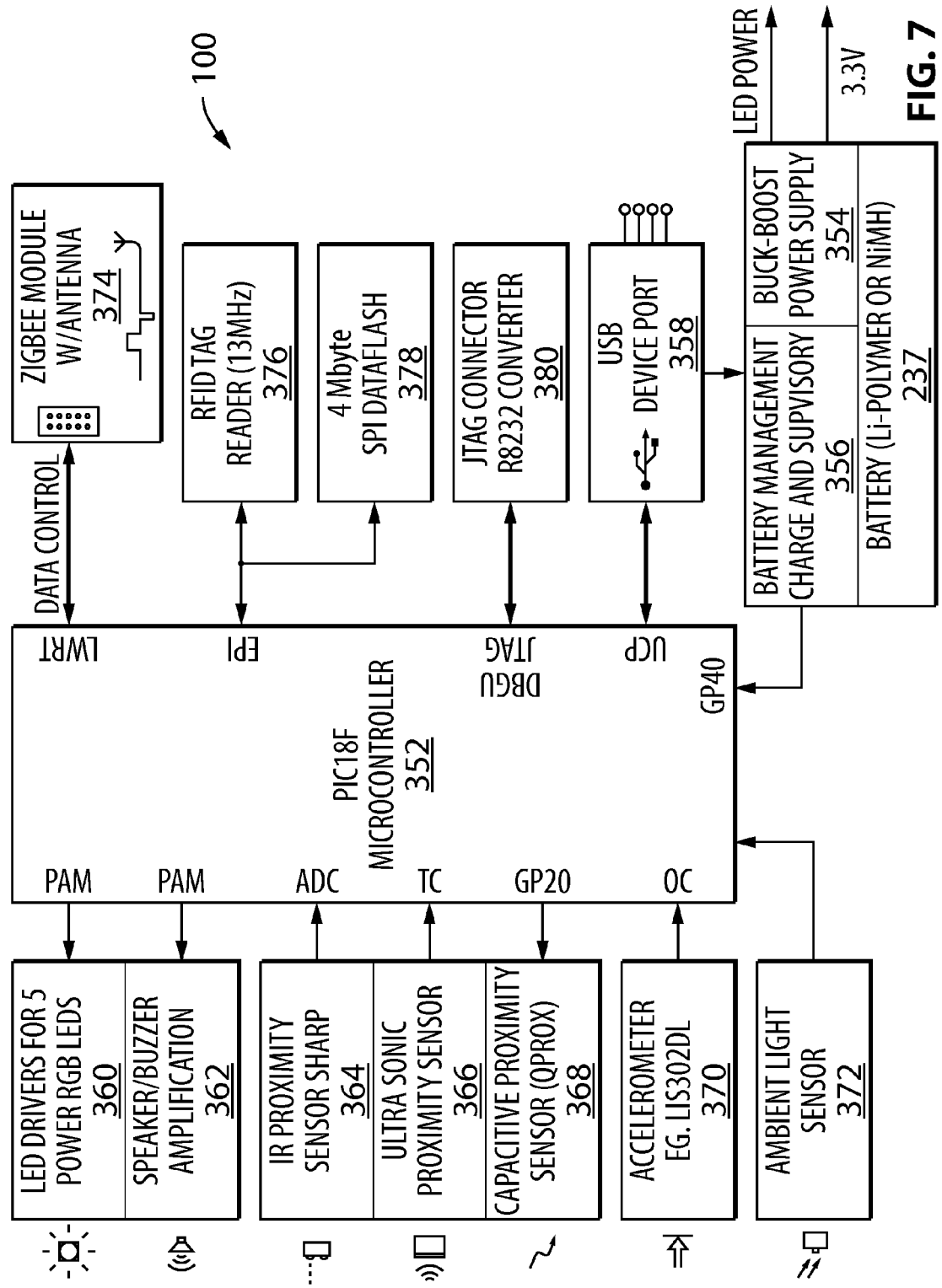
FIG. 7 is a system block diagram of the electronic components employed in the stimulant target unit of FIG. 1, according to a non-limiting embodiment.

FIG. 7 shows a system block diagram of the major electronic components of the stimulant target unit 100. The stimulant target unit 100 includes a central microcontroller 352, such as a Microchip® PIC18F, which is powered by the batteries 237 via a buck-boost power supply 354 that is supervised by a battery management circuit 356. A universal serial bus port (USB) 358 is connected to the microcontroller 352 and the battery management circuit 356. In addition, the microcontroller is connected to memory 378 and a JTAG connector 380.

The central microcontroller 352 controls the device or devices configured to provide a stimulus to the user. For example, the stimulus LEDS 118 are controlled by the central microcontroller 352 via LED drivers 360 and an ambient light sensor 372, which is used to control the power supplied by LED drivers 360. The stimulant target unit 100 can have the capability of generating different colors when red, green and blue (RGB) LEDs 118 are employed. This allows software executed by the microcontroller 352 to generate different colors of stimulating light. This capability allows the user to program training routines where, for example, only red lights are deactivated and green ones are not. This allows the system to test user reaction and speed of recognition, or it allows the user to exercise their cognitive and memory skills by activating only certain color lights that may come on momentarily with various other colors.

The intensity of the light generated by the LEDs 118 is automatically adjustable by the microcontroller to accommodate various ambient light conditions. In particular, it is desirable to have very visible light in direct sunlight. Thus, the ambient light sensor provides feedback for adapting the intensity of the LEDs 118.

A speaker with amplification circuit 362 is also connected to the microcontroller 352 for providing audio feedback and/or audio stimulus to users.

The microcontroller 352 is also connected to a contact sensor, which may be, for example, an accelerometer 370 configured to sense an impact (e.g. from contact with the user or from contact with a projectile directed at the upper shell 102). For example, the accelerometer 370 can be configured to determine the impact force due to an impact sustained by the stimulant target unit 100 based on an acceleration of the stimulant target unit 100 in response to the impact. The microcontroller 352 is programmed to register triggering of the contact sensor if the determined impact force falls within a selected range of impact forces. The accelerometer 370 can be a three-axis accelerometer. Although the contact sensor is shown as an accelerometer, it is understood that any suitable device for measuring the impact force sustained by the stimulant target unit 100 is contemplated as the contact sensor.

Because the upper shell 102 is what is impacted so as to trigger the contact sensor (e.g. the accelerometer 370) upper shell 102 may also be referred to as the primary contact member 102.

The microcontroller 352 may also be connected to at least one of an infrared proximity sensor 364, an ultrasonic proximity sensor 366, and a capacitive proximity sensor 368.

The microcontroller 352 may also be connected to a wireless personal area network (PAN) communication controller (with antenna) 374, and a radio frequency identification (RFID) tag reader 376, which may be provided by a commercial Zigbee or IEEE 802.15.4 personal area network integrated circuit (IC). The purpose of these components will become clearer in conjunction with an appreciation of the system controller 400.

Figure 8:
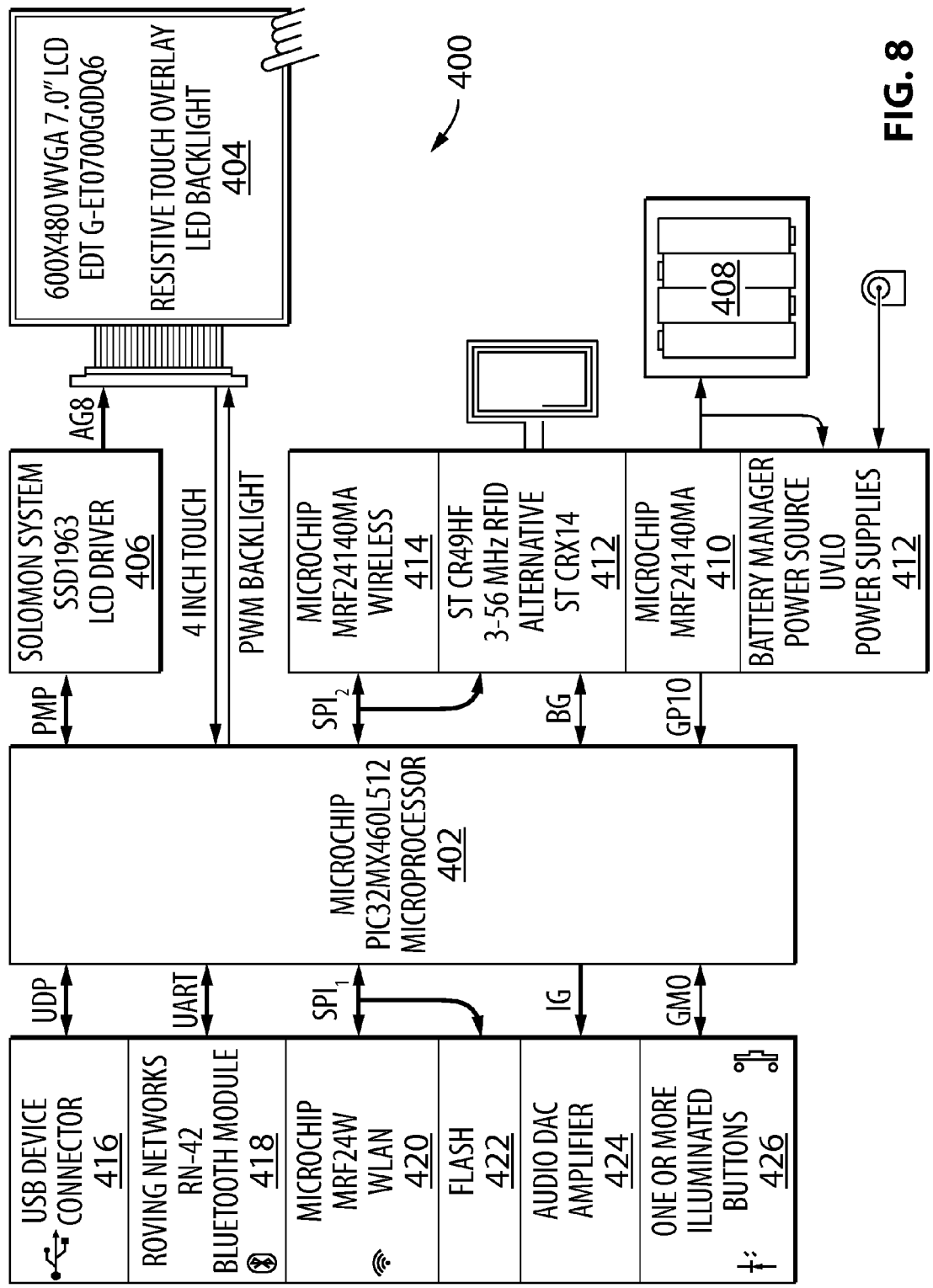
FIG. 8 is a system block diagram for the electronic components employed in a system controller that manages multiple stimulant target units as part of a cohesive network, according to a non-limiting embodiment.

FIG. 8 shows a system block diagram of a system controller 400. The system controller 400 has a central microprocessor 402, such as Microchip® PIC32MX460L512, which is connected to a touch sensitive liquid crystal display (LCD) screen 404 via an LCD driver 406. The system controller 400 is also powered by rechargeable batteries 408 via battery charge and management circuits 410 and 412. An RFID tag reader/writer 412 and a personal area network controller 414, such as a Microchip® MRF24J40MA Zigbee transceiver, are also connected to the microprocessor 402. Likewise, the microprocessor 402 is connected to a universal serial bus port 416; a Bluetooth circuit 418; a wireless LAN circuit 420; memory 422; an audio controller 424; and one or more illuminated push buttons 426.

Figure 9:
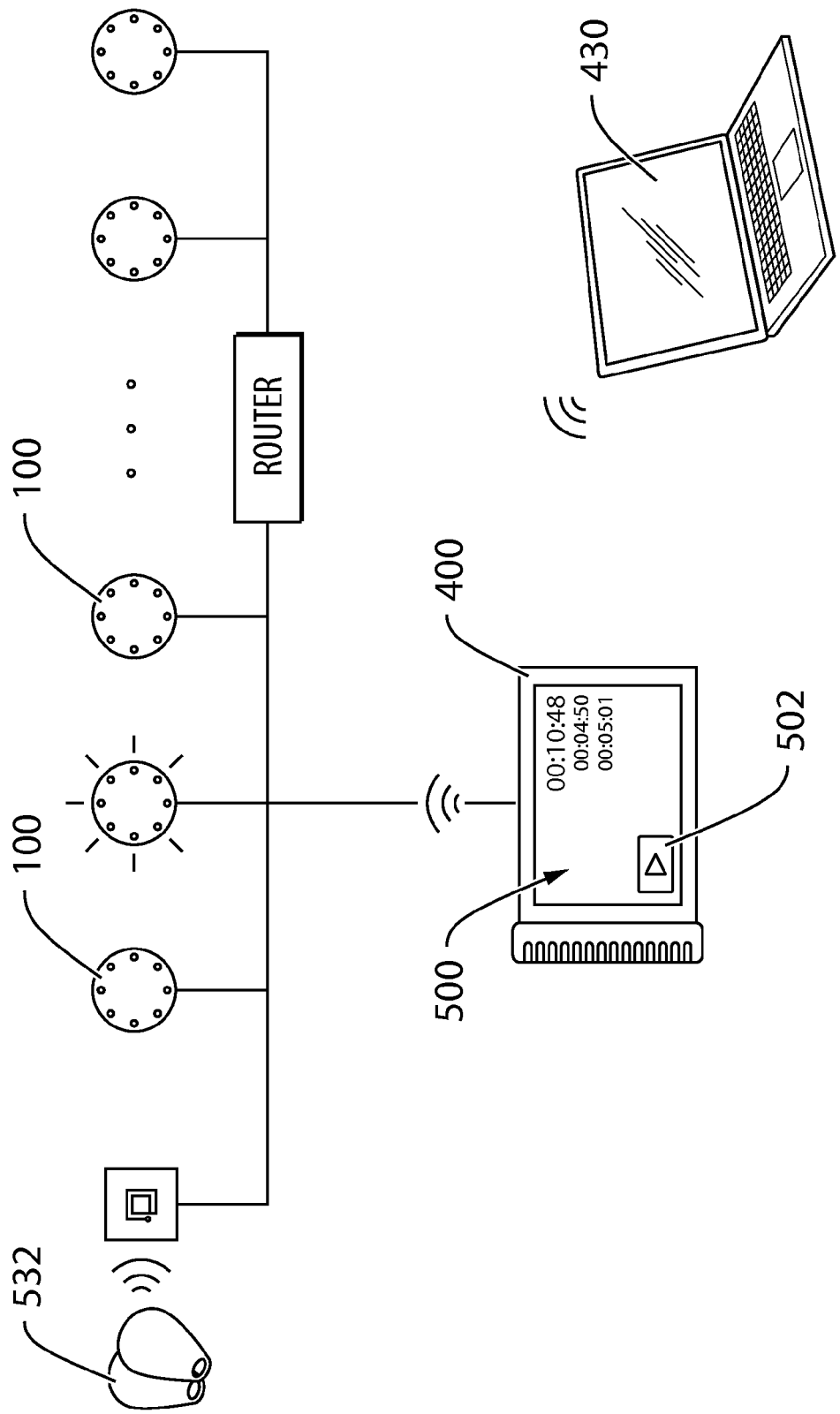
FIG. 9 is a schematic network diagram of a training system comprising the system controller shown in FIG. 8 with multiple stimulant target units shown in FIG. 1, according to a non-limiting embodiment.

As shown in FIG. 9, the system controller 400 may function as the coordinator of a ZigBee (or similar) wireless network where the stimulant target units 100 function as ZigBee end devices. The system controller 400 initiates a wireless network and discovers the number of stimulant target units 100 within reception range. The system controller 400 also receives requests from recently turned on stimulant target units 100 to join the system managed by the system controller 400. This enables a user to rapidly and dynamically configure the number of stimulant target units 100 that comprise the training system.

Once the wireless network is established, communication occurs wirelessly over RF channel(s). The system controller 400 maintains a set of instructions, that may be entered in or otherwise programmed by the user as described in greater detail below, that can sequence: (i) which stimulant target units 100 should light up (and if applicable or desired, the colour of light); (ii) the selected range of impact forces within which an impact or "hit" will be registered by the microcontroller 352; and (iii) the time delay to the activation of the next stimulant target unit 100 in the sequence. The time delay may also be zero, in which case two stimulant target units 10 will light up together. Thus, communicating over the wireless RF channel(s), the system controller 400 signals a specific stimulant target unit 100 to light up. In turn, when a specific stimulant target unit is actuated it wirelessly signals the system controller 400 accordingly. The system controller 400 can measure the time delay between the stimulus and response, or, for more precision, each stimulant target unit 100 can measure the user response time and transmit it to the system controller 400 for recordal. Optionally, the system controller 400 will also record the time of each 'hit'. Optionally, the system controller 400 will also record the time of each miss, where a miss is determined to occur if the stimulant target unit 100 is illuminated for more than a selected amount of time without registering a 'hit'.

The system controller 400 may be programmed through conventional keyboard input, via touch screen, keypad input or any other suitable input means. For example, as shown in FIG. 9, the system controller 400 can interface with a personal computing device, such as a laptop 430, via the wireless LAN 420 or universal serial bus 416. The laptop 430 can execute a more elaborate user interface program. A graphical user interface 500 can be implemented on the system controller 400 and generated for display on LED screen 404. The training routine or sequence can be activated by pressing a virtual start/stop button 502. The name of the user performing the routine may be automatically known from a pre-assigned RFID tag 532 worn by the user.

Figure 10:
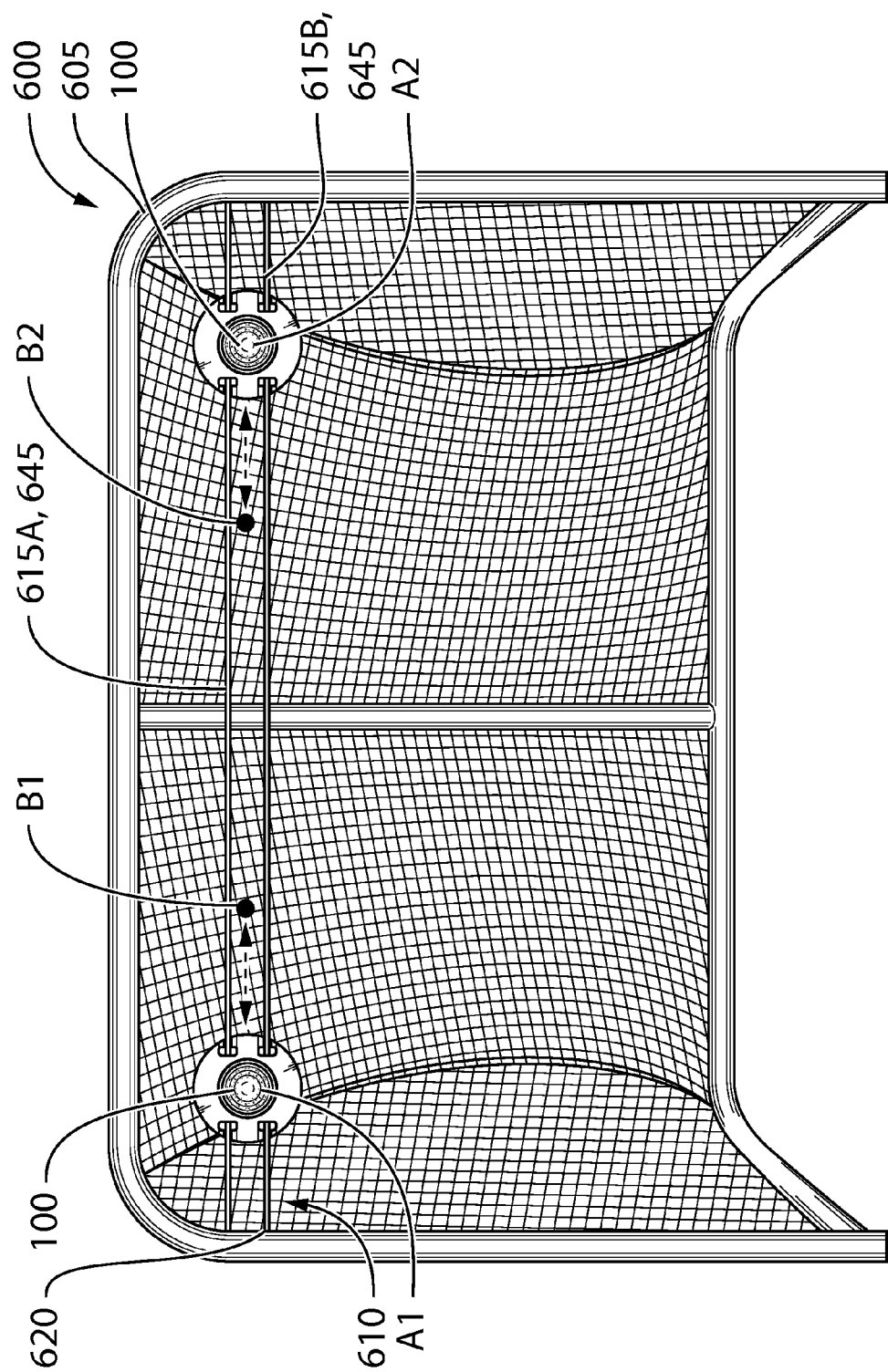
FIG. 10 shows an example set of stimulant target units used for hockey skills training having a protective cover and a mounting structure, according to a first set of non-limiting embodiment.

FIG. 10 depicts an example set of stimulant target unit assemblies 600 for hockey skills training. Each assembly 600 includes one of the stimulant target units 100, a protective cover 625 (shown in FIG. 11) positioned for covering the stimulant target unit 100, and a mounting structure 610 that connects the stimulant target to a support structure 605, which in this case is a hockey net.

The protective cover 625 is configured to withstand an impact from a projectile, which can be at least one of a hockey puck, a round of non-lethal ammunition (such as Simunition™) and a round of lethal ammunition. For example, the protective cover 625 can be made from an impact resistant material, such as a polycarbonate. The protective cover 625 can be manufactured in a variety of ways, including using vacuum forming.

Without the protective cover 625, the primary contact member 102 is configured to transmit a force from an impact from a user or from a projectile within a first range of impact forces to the contact sensor so as to trigger the contact sensor (i.e. accelerometer 370) sufficiently that the controller 325 registers the impact and illuminates the LEDs. As noted above the protective cover 625 is configured to cover the stimulant target unit 100 and to be spaced by a selected spacing from the primary contact member 102. The spacing is shown at G in FIG. 12D, and is selected to permit the protective cover 625 to receive an impact and transmit the impact to the primary contact member 102 to trigger the contact sensor 370 over a second range of impact forces that is higher than the first range of impact forces (including, for example, the force from a hockey puck at 100 mph impact-ing the protective cover, or for example, the force from an impact by training ammunition fired from a firearm against the protective cover during a tactical training exercise). As a result, the stimulant target unit 100 can be used without the protective cover 625 for a first selected variety of activities in which the forces are in a first, lower range, such as a training exercise in which the user would tap the device with his/her hand, and also can be used with the protective cover 625 for a second selected variety of activities in which the forces are in a second, higher range of impact forces, such as a training exercise in which the user takes shots at the target units 100 with a hockey puck. Utilizing the target unit 100 without the protective cover 625 for such an activity could eventually lead to marking up of the primary contact member 102, rendering it more difficult to see the LEDs within the unit 100, or could lead to mechanical failure of the primary contact member 102. By contrast, if the protective cover 625 becomes damaged or is no longer sufficiently transparent to see the LEDs within the stimulant target unit 100 that it is covering, it can be discarded and replaced relatively easily.

Figure 12B:
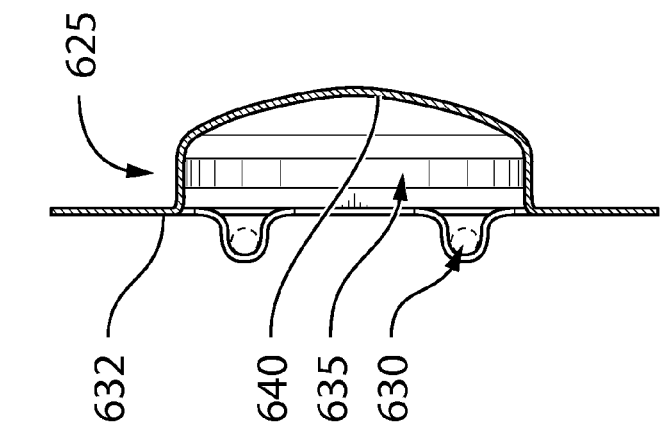
FIG. 12B is a cross-section view of the protective cover shown in FIG. 11, according to a first set of non-limiting embodiments.
Figure 12A:
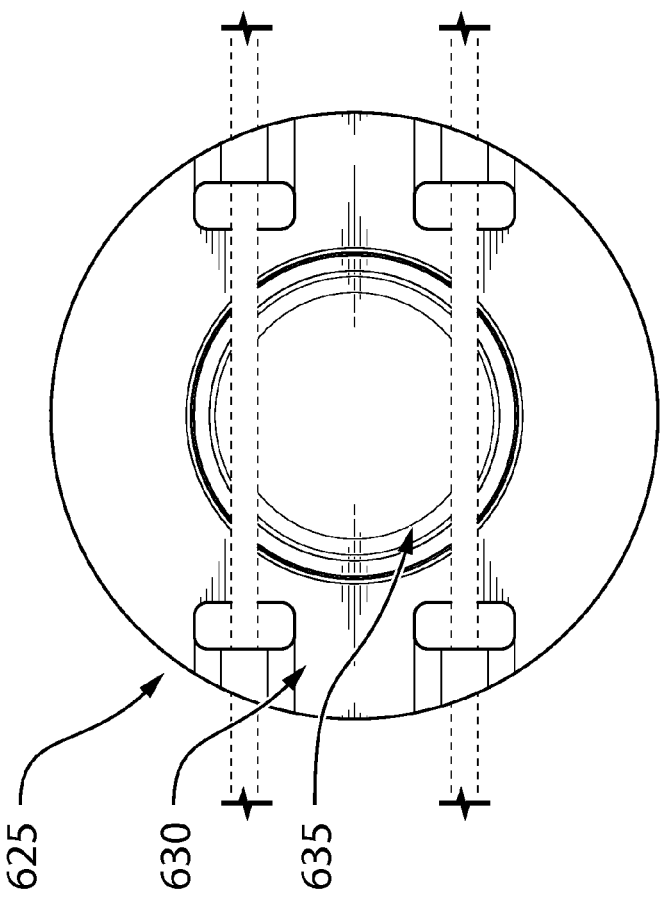
FIG. 12A is a top view of the protective cover shown in FIG. 11, according to a first set of non-limiting embodiments.
Figure 12C:
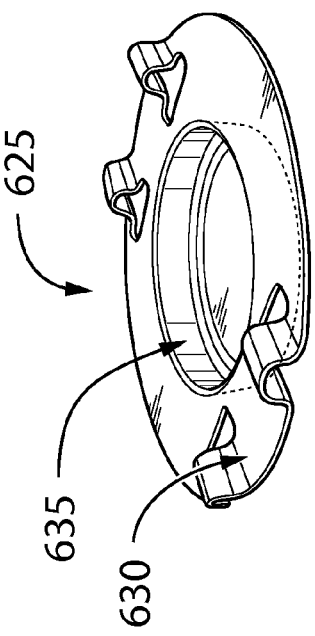
FIG. 12C is a perspective bottom view of the protective cover shown in FIG. 11, according to a first set of non-limiting embodiments.
Figure 12D:
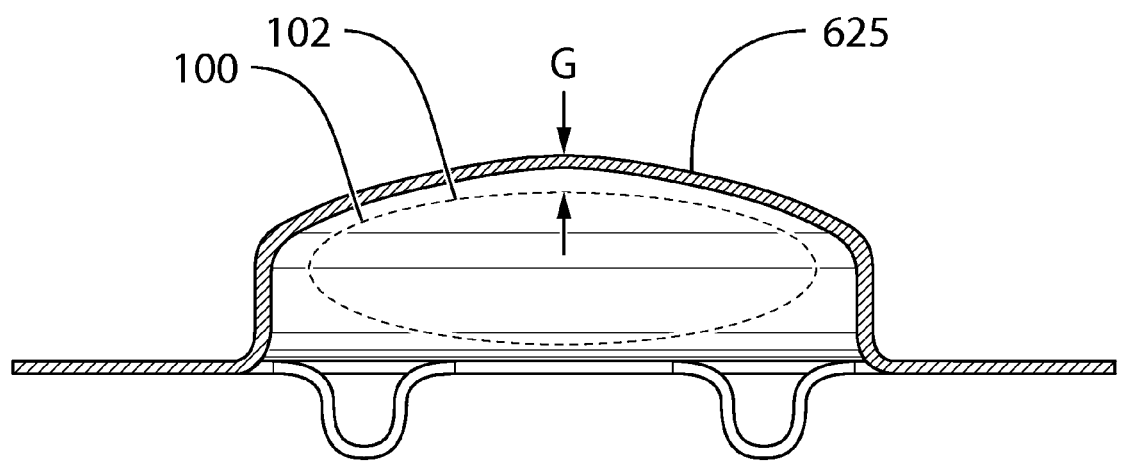
FIG. 12D is a sectional elevation view of the protective cover shown in FIG. 11, showing a dashed outline of the stimulant target unit contained within.

The mounting structure 610 includes elastic cords 615a, 615b and support attachments 620. As shown in FIGS. 12A to 12C, the protective cover 625 is configured to connect to the mounting structure 610. The protective cover 625 includes grooves 630 configured to engage the elastic cords 615a, 615b. The protective cover 625 also includes a cavity 635 sized to hold the stimulant target unit 110 therein. The grooves 635 project away from rear cover face 632. The protective cover 625 is configured such that the stimulant target unit 100 rests in the cavity 635 is nested between the inner face 640 (FIG. 12B) of the cavity 635 and the elastic cords 615a, 615b. The grooves 635 may be sized such that the elastic cords 615a, 615b frictionally engage the grooves 635, which may help prevent shifting of the stimulant target unit 100 along either one of the elastic cords 615a, 615b during an impact to the protective cover 625 from a projectile directed at the stimulant target unit 100.

In some embodiments, the cavity 635 includes at least one translucent portion 650 to enable the user to see the visual stimulus (e.g., produced by stimulus LEDS 118).

Each of the stimulant target units 100 is connected to the support structure 605 via the mounting structure 610. As stated above the mounting structure 605 includes elastic cords 615a, 615b and support attachments 620. The support attachments 620 can include any fastener or retaining structure suitable for connecting the elastic cords 615a, 615b to the support structure 605. For example, the attachments 620 can include hooks that are sized and otherwise configured to grasp the support structure 605 in the desired position and orientation.

In some embodiments, the mounting structure 610 may be configured to position the stimulant target unit 100 in at least one of a plurality of positions and a plurality of orientations in respect of the support structure 605. For example, the grooves 630 may be configured to enable the stimulant target units 100 to slide along the elastic cords 615a, 615b from positions A1, A2 to positions B1, B2, respectively (FIG. 10).

If the stimulant target unit 100 were rigidly connected to the support structure 605, the impact force from an impact to the structure that is within the selected range of impact forces could trigger the contact sensor and the microcontroller 352 would then incorrectly register an impact or "hit" to the stimulant target unit 100 (i.e., register a "false positive").

In order to inhibit the transmission of force from an impact to the support structure 605, so as to avoid the occurrences of "false positives", the mounting structure 610 includes a vibrational isolator 645. The vibrational isolator 645 is configured to inhibit the transmission of force from an impact to the supporting structure that is within the selected range of impact forces to trigger the contact sensor (e.g., the accelerometer 370) of the stimulant target unit 100 to prevent triggering the contact sensor.

Figure 11:
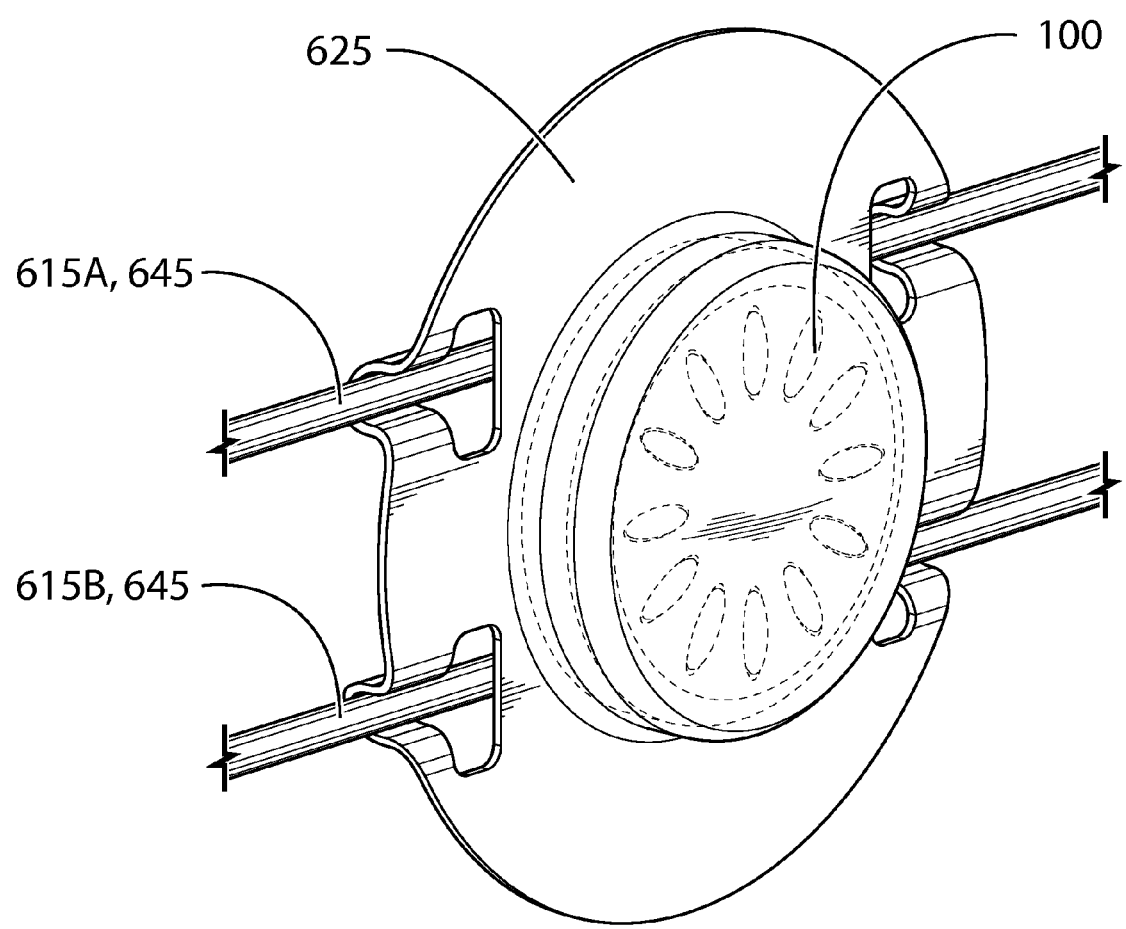
FIG. 11 is a an enlarged view of a stimulant target unit including the protective cover and the mounting structure of FIG. 10, according to a first set of non-limiting embodiment.

The vibration isolator 645 can include at least one of a resilient member and a damping member. For example, as shown in FIGS. 10 and 11, the vibration isolator 645 include elastic cords 615a, 615b as resilient members that store at least a portion of the impact force from an impact to the support structure 605 as potential force. In some embodiments, the resilient member and the damping member are provided by the same component. For example, in some embodiments, the elastic cords 615a, 615b are configured to frictionally engage with the grooves 630 during an impact to the structure 605 and dissipate at least a portion of the impact force from the impact to the structure 605 through friction, thereby providing at least some damping. In such embodiments, the elastic cords 615a, 615b may include a textured covering configured to frictionally engage with the grooves 630. In some embodiments, the resilient member and the damping member are provided by separate components.

Figure 13:
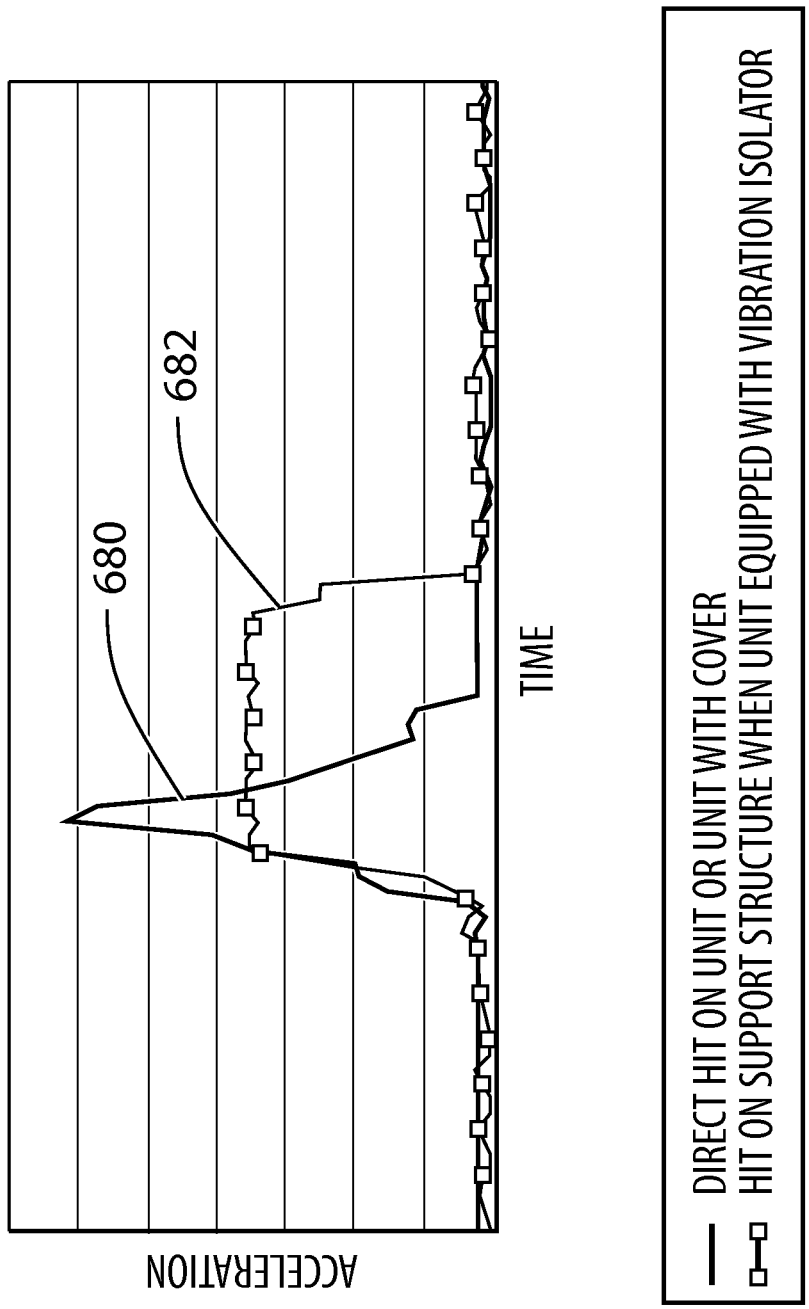
FIG. 13 is a graph showing a curve for the acceleration measured when a direct hit occurs on the stimulant target unit or on the protective cover and a curve for the acceleration measured when a hit occurs on the support structure for the stimulant target unit.
Figure 14:
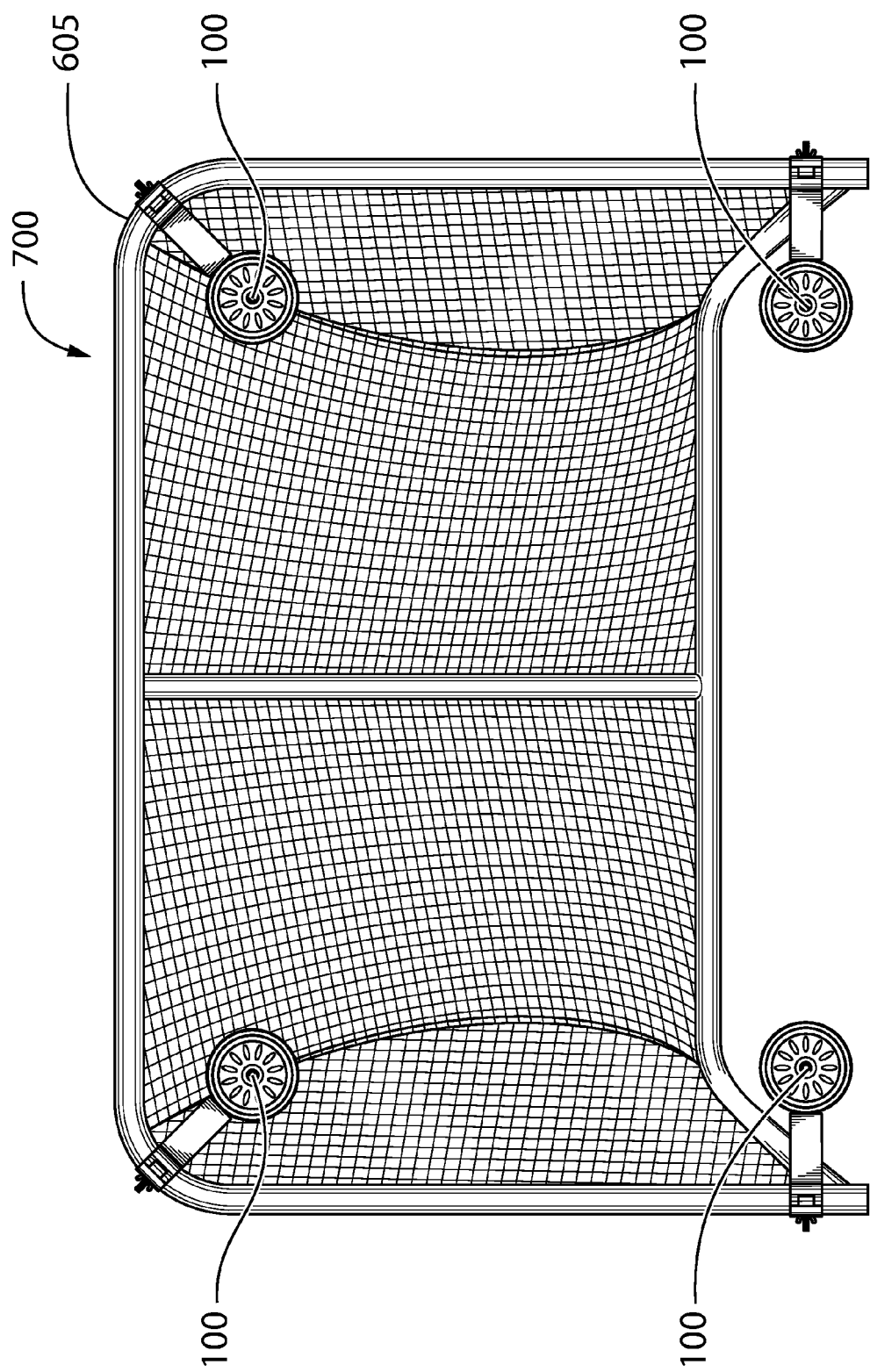
FIG. 14 shows another example set of stimulant target units used for hockey skills training having a protective cover and a mounting structure, according to a second set of non-limiting embodiments.

FIG. 13 shows a graph with two curves on it. The first curve, shown at 680, illustrates the acceleration detected by the accelerometer 370 on the stimulant target unit 100 when a direct hit or impact occurs by a projectile such as a puck or a round of ammunition, on the unit 100 or on the protective cover 625. The second curve, shown at 682, illustrations the acceleration detected by the accelerometer 370 when an impact from the same projectile occurs on the support structure 605. As can be seen, the portion of the curve 680 representing the impact on the protective cover 625 or on the unit 100 itself has roughly two times the peak magnitude, and is of shorter duration than the portion of the curve 682 representing the impact on the support structure 605. As a result of this difference in the shapes of the curves 680 and 682 the microcontroller 352 can, relatively easily determine whether an impact was a direct impact on the unit 100 or cover 625 (in which case it may, for example, illuminate the LEDs), or whether it was an indirect impact on the support structure 605, (in which case, it will not illuminate the LEDs, or it may illuminate the LEDs in a different colour to indicate that an indirect impact was detected). In this way, the system controller 400 can immediately give feedback of hits and misses (at least misses that are detected as indirect hits). For the purposes this disclosure, it will be noted that, even in situations where the stimulant target unit 100 does not illuminate the LEDs, it is still providing feedback. For example, the microcontroller may take a ratio of the peak acceleration over the total duration of the measured impact event, and will illuminate the LEDs to indicate an impact only if the determined ratio exceeds a selected value. The data in the graph in FIG. 13 would yield a ratio for the curve 680 that is approximately three times larger than the ratio for the curve 682. As a result, it would be relatively easy for the microcontroller 352 to determine which impacts occurred on the unit 100 or the protective cover 625 and which did not, with little risk of registering false positives.

FIGS. 14 to 16B depict a second example set of stimulant target units 700. Each of the stimulant target units 100 is connected to the support structure 605 by mounting structures 755 (also referred to individually as "mounting structure 755"). Each of the stimulant target units 100 includes a protective cover 760 configured to retain the stimulant target unit 100. Similarly to the protective cover 625, the protective cover 760 includes a cavity (not shown) sized to hold the stimulant target unit 100 therein, while maintaining the spacing G from the primary contact member. For example, the protective cover 760 can be formed from two halves, each having a recess sized to hold a portion of the stimulant target unit 100. When brought together the recess in each half forms the cavity configured to retain the stimulant target unit 100. The two halves may be attached to each other using a cover rim 765 or any other suitable component or combination of components.

Similarly to the protective cover 625, in some embodiments, the cavity of the protective cover 760 includes at least one translucent portion 780, which enables the user to see the visual stimulus (e.g., produced by stimulus LEDS 118).

Similarly to the protective cover 625, the protective cover 760 is configured to withstand an impact from a projectile. The projectile can be at least one of a hockey puck, a round of non-lethal ammunition (such as Simunition™) and a round of lethal ammunition. For example, the protective cover 760 can be made from an impact resistant material, such as a polycarbonate. The protective cover 760 can be manufactured in a variety of ways, including using vacuum forming, and manufactured in a variety of ways.

Figure 15:
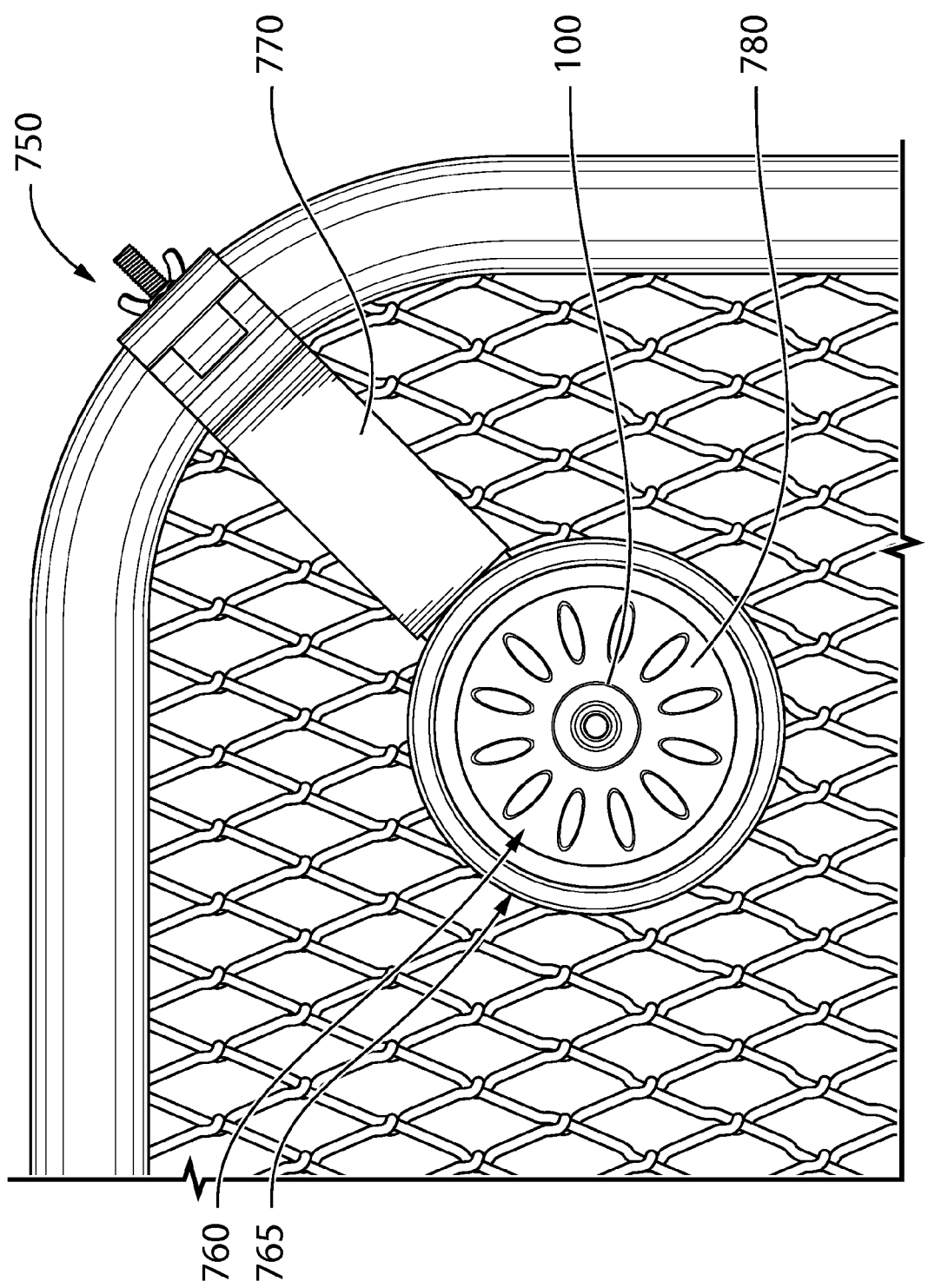
FIG. 15 is a front view of one of the stimulant target units including the protective cover and mounting structure of FIG. 14, according to a second set of non-limiting embodiments.
Figure 16A:
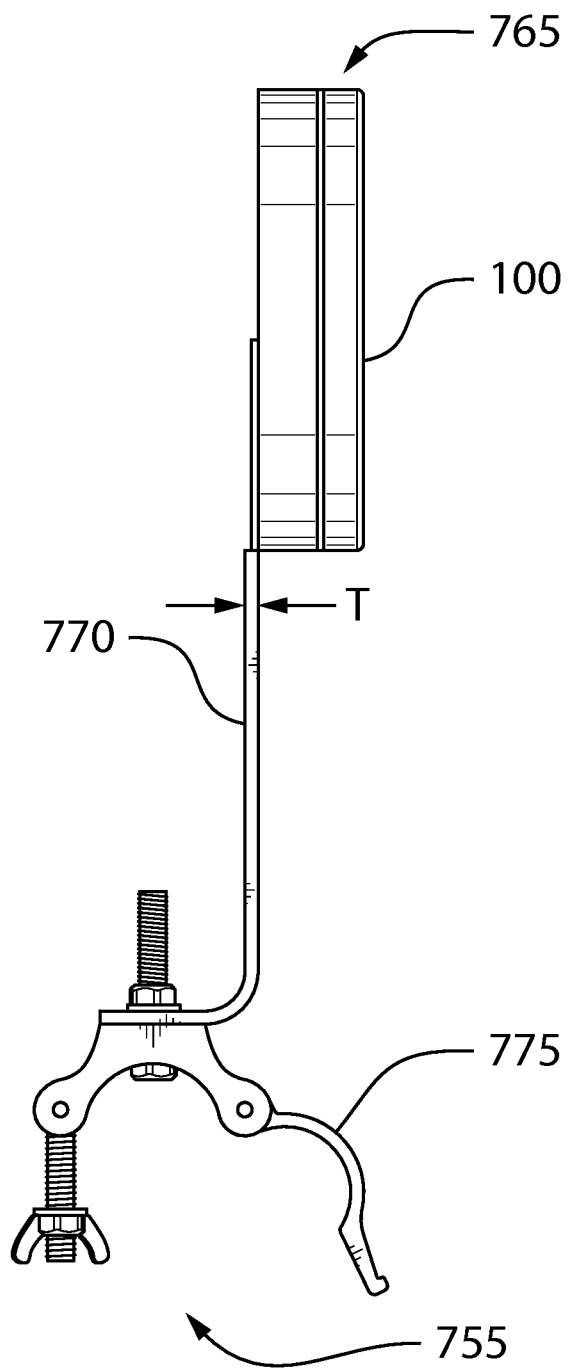
FIG. 16A is a side view of the stimulant target unit including the protective cover and mounting structure as shown in FIG. 15, according to a second set of non-limiting embodiments.
Figure 16B:
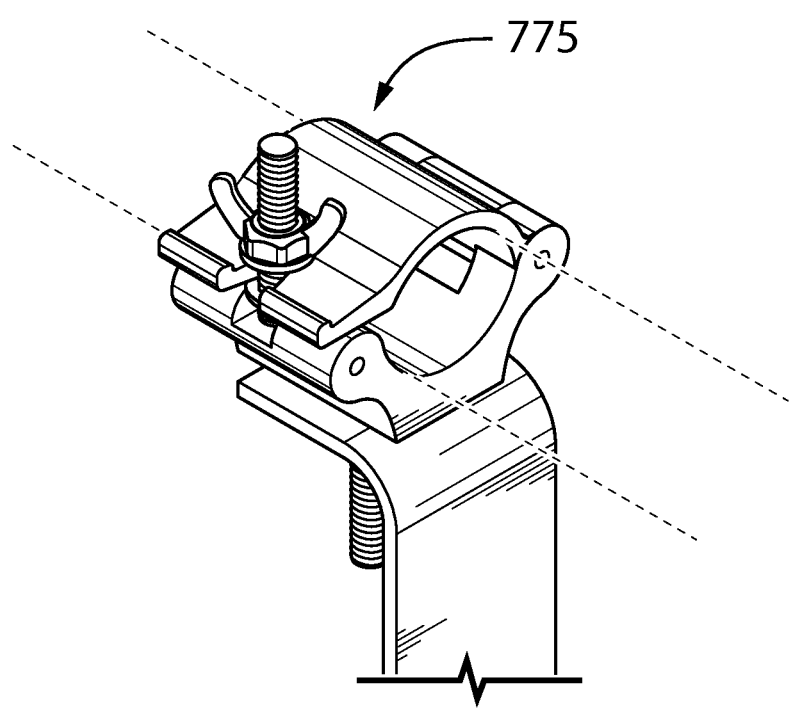
FIG. 16B is an enlarged view of the mounting structure shown in FIG. 15, according to a second set of non-limiting embodiments.

As shown in FIGS. 15, 16A and 16B, the mounting structure 755 includes a mounting arm 770 and clamping structure 775. The mounting arm 770 is configured as a vibrational isolator in that the mounting arm 770 is configured as a flat spring that stores at least a portion of the impact force from an impact to the support structure 605 as potential force. As a result, the mounting arm 770 inhibits the transmission of impact force from an impact to the supporting structure 605 to the contact sensor of the stimulant target unit 100. If the impact force from the impact to the supporting structure 605 is within the selected range of impact forces that trigger the contact sensor, the mounting arm 770 may help to avoid the occurrence of incorrect registrations of an impact or "hit" to the stimulant target unit 100 by the microcontroller 352.

The mounting arm 770 can be configured to absorb a desired amount of impact force. For example, the cross-sectional thickness, T (FIG. 16A), can be increased or decreased to produce the resiliency required to absorb the desired amount of impact force.

Figure 17:
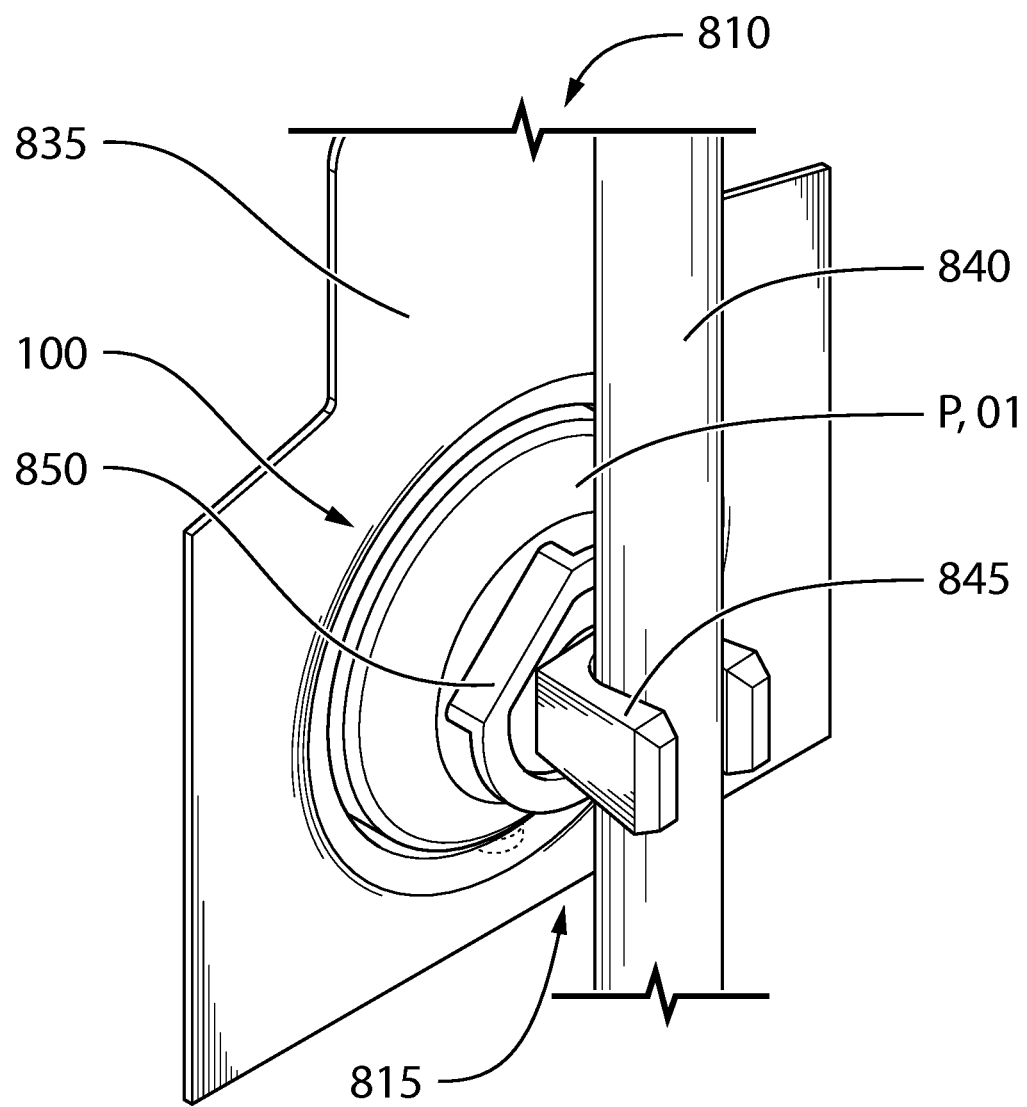
FIG. 17 is a rear perspective view of a stimulant target unit including a protective cover and a mounting structure in a first orientation in respect of a support structure, according to a third set of non-limiting embodiments.
Figure 18:
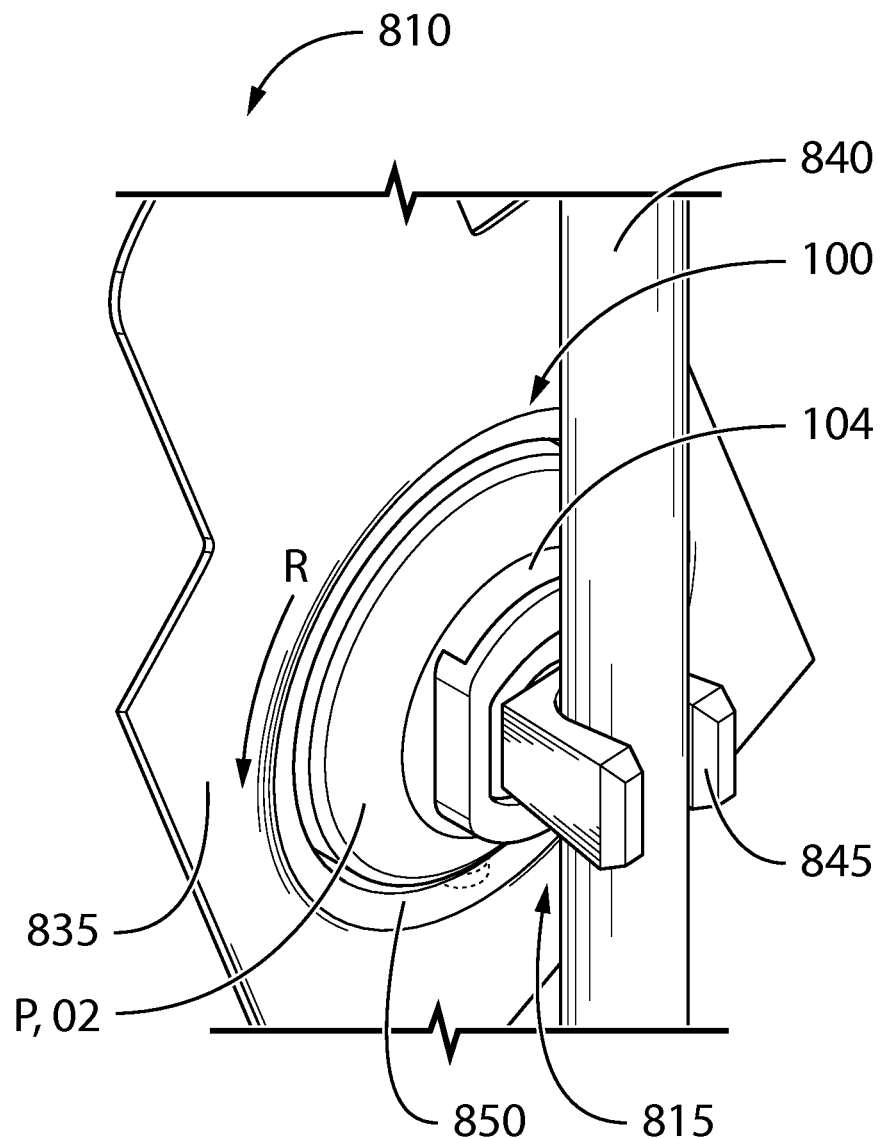
FIG. 18 is a rear perspective view of a stimulant target unit including a protective cover and a mounting structure in a second orientation in respect of a support structure, according to a third set of non-limiting embodiments.

FIGS. 17 and 18 depict another example of the stimulant target unit 100 including a protective cover 810 and a mounting structure 815. Similarly to the protective cover 625, the protective cover 810 is configured to withstand an impact from a projectile, which can be at least one of a hockey puck, a round of non-lethal ammunition (such as Simunition™) and a round of lethal ammunition. For example, the protective cover 810 can be made from an impact resistant material, such as a polycarbonate. The protective cover 810 can be manufactured in a variety of ways, including using vacuum forming, and manufactured in a variety of ways.

Figure 19B:
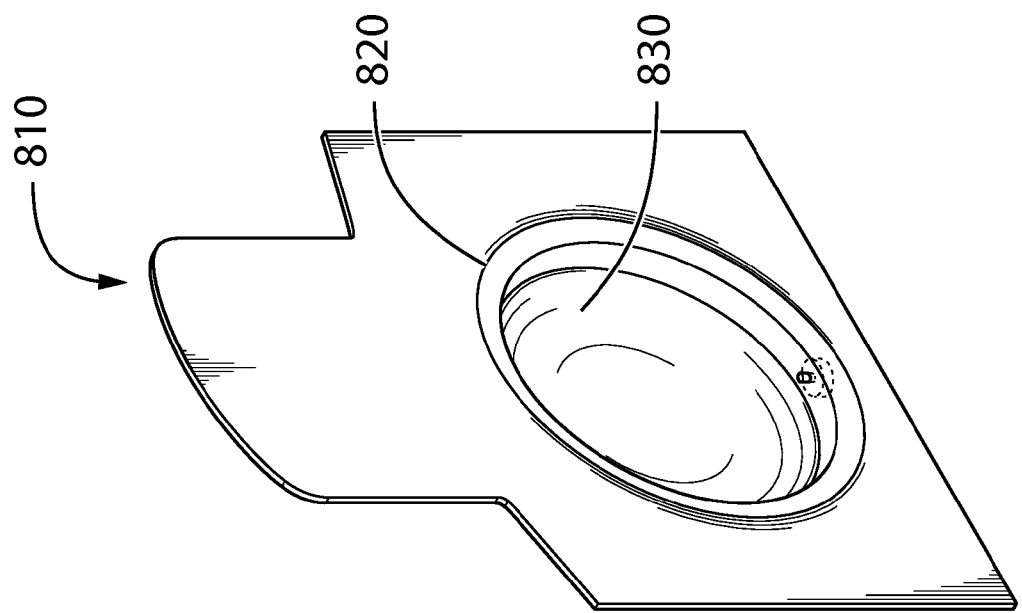
FIG. 19B is a rear view of the protective cover shown in FIG. 17, according to a third set of non-limiting embodiments.
Figure 19A:
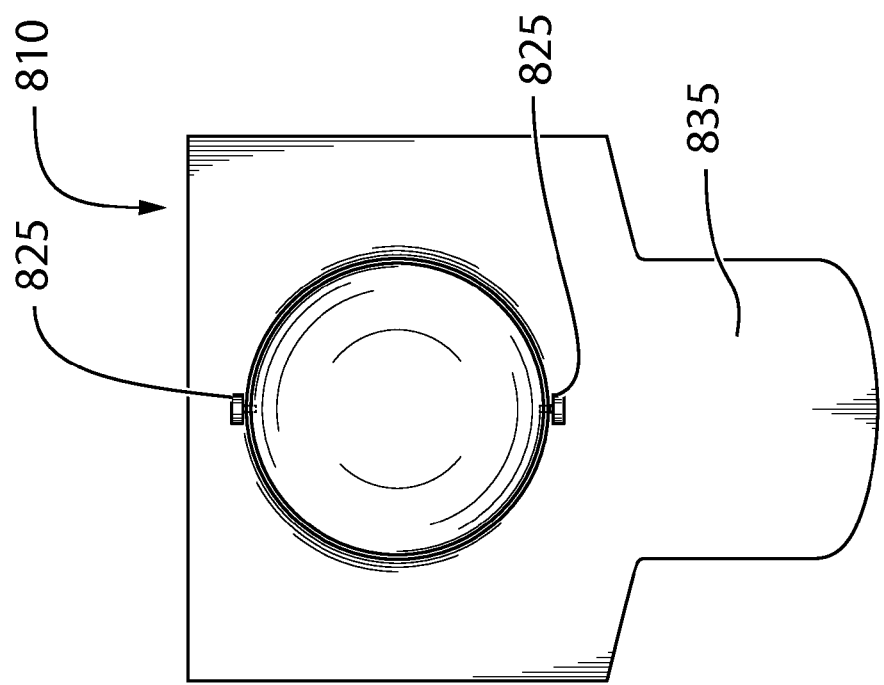
FIG. 19A is a top view of the protective cover shown in FIG. 17, according to a third set of non-limiting embodiments.

The protective cover 810 also includes a cavity 820 (FIGS. 19A, 19B) that is sized to hold the stimulant target unit 110 therein. The protective cover 810 also includes at least one fastener configured to couple the stimulant target unit 100 to the protective cover 810. For example, as shown in FIG. 19A, the protective cover 810 includes fasteners 825, shown as screws that are threaded through holes (not shown) in the protective cover 810, that are configured to engage at least one exterior surface of the stimulant target unit 100, such as exterior surface 107 of the rim 106 (FIG. 1), and clamp the stimulant target unit 100 therebetween. Although the fasteners 825 are shown as screws, it is understood that any device or component that is configured to couple the stimulant target unit 100 to the protective cover 810 within the cavity 820 is contemplated.

Similarly to the protective cover 625, in some embodiments, the cavity 820 includes at least one translucent portion 830 to enable the user to see the visual stimulus (e.g., produced by stimulus LEDS 118).

The protective cover 810 may have a variety of shapes. For example, the protective cover 810 includes an extension 835 that may provide a space for markings, such as brand logos and/or training instructions.

Figure 20A:
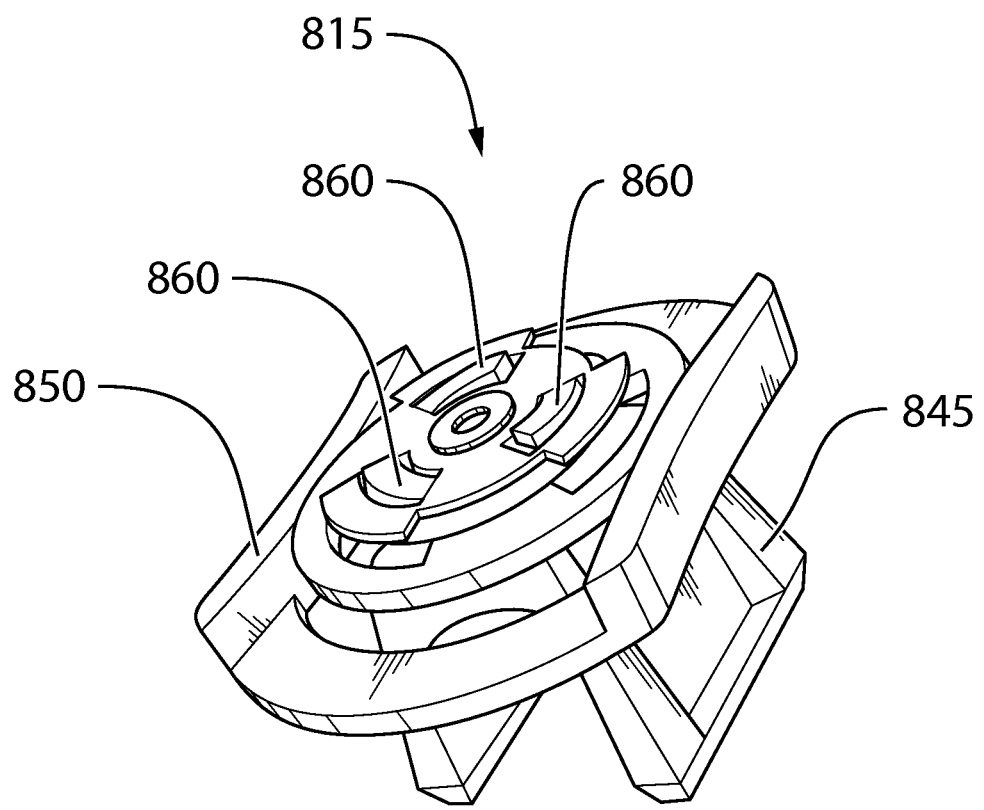
FIG. 20A is a perspective view of the mounting structure shown in FIG. 17, according to a third set of non-limiting embodiments.
Figure 20B:
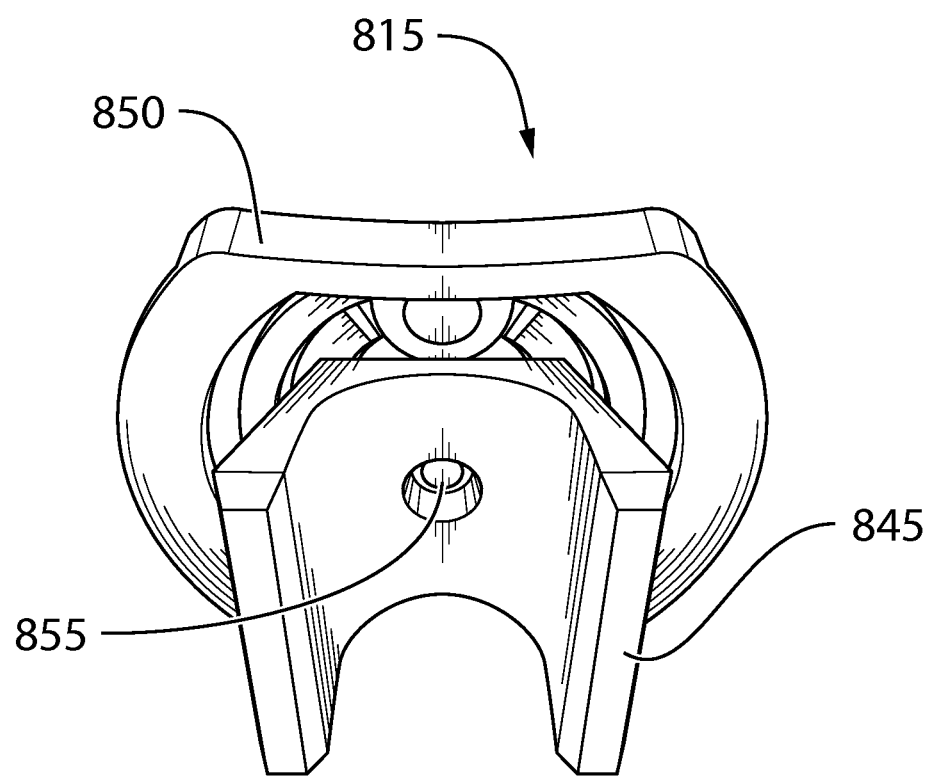
FIG. 20B is a rear view of the mounting structure shown in FIG. 17, according to a third set of non-limiting embodiments.

The mounting structure 815 is configured to connect the stimulant target unit 100 to a support structure 840. The mounting structure 815 includes a connector 845 and interface member 850 (FIGS. 20A, 20B). The connector 845 attaches to the support structure 840 and the interface member 850 attaches to the stimulating target unit 100. As shown in FIGS. 17 and 18, the interface member 850 attaches to the lower shell 104 of the housing 105 of the stimulant target unit 100 via mounting fastener 855 (FIGS. 20A, 20B).

The mounting structure 815 includes a vibrational isolator in the form of the interface member 850. The interface member 850 includes resilient members 860 that are configured to inhibit the transmission of force from an impact to the supporting structure 840 that is within the selected range of impact forces to trigger the contact sensor (e.g., the accelerometer 370) of the stimulant target unit 100 to prevent triggering the contact sensor. The resilient members 860 behave similarly to the mounting arm 770 in that the resilient members 860 behave as flat springs that store at least a portion of the impact force from an impact to the support structure 840 as potential force. As a result, the resilient members 860 inhibit the transmission of impact force from an impact to the supporting structure 840 to the contact sensor of the stimulant target unit 100. If the impact force from the impact to the support structure 840 is within the selected range of impact forces that trigger the contact sensor, the resilient members 860 may help to avoid the occurrence of incorrect registrations of an impact or "hit" to the stimulant target unit 100 by the microcontroller 352. Although three resilient members 860 are shown (FIG. 20A), the interface member 850 can include any suitable number of resilient member 860 to store the desired amount of impact force from an impact to the structure 840.

The mounting structure 815 may be configured to position the stimulant target unit 100 in at least one of a plurality of positions and a plurality of orientations in respect of the support structure 840. For example, as shown in FIGS. 17 and 18, the stimulant target unit 100 is in a first orientation, O1, in respect of the support structure 840. A point, P, will be used to track the change in orientation of the stimulant unit 100 from orientation O1 to orientation O2 (FIG. 18). The mounting structure 815 can be configured such that the interface member 850 is rotatable in respect of the connector 845, which is connected to the support structure 840. As shown in FIG. 18, by rotating the interface member 850 in direction, R, the orientation of the stimulant target unit 100 can be changed from orientation O1 to orientation O2.

Figure 21:
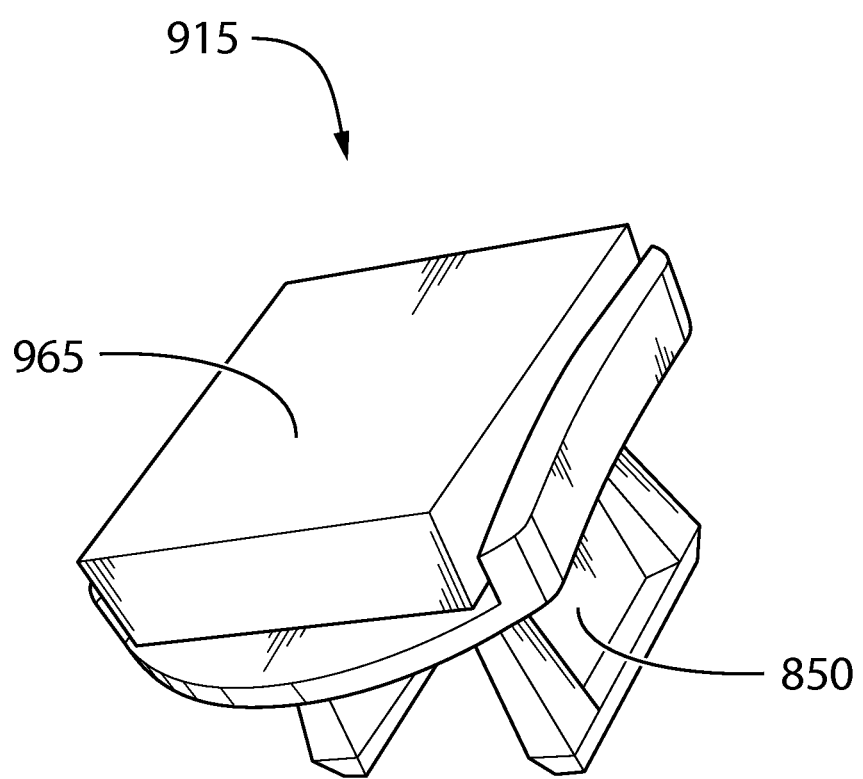
FIG. 21 is a perspective view of a mounting structure including a damping member that includes a deformable member, according to a non-limiting embodiment.

Although the vibration isolator of the mounting structure 815 includes resilient members, in some embodiments, the vibration isolator can include a damping member in place of the resilient members 860. For example, FIG. 21 shows an example modification of the mounting structure 815, as a mounting structure 915, in which the interface member 850 includes a deformable member 965 that is configured to absorb and dissipate at least a portion of the impact force from an impact to the support structure 840. The deformable member 965 is manufactured from a material having damping properties, such as a visco-elastic polymer that can absorb and dissipate, as heat, at least a portion of the impact force. It is understood that any suitable material having damping properties is contemplated.

Any of the protective covers described herein may be combined with any of the mounting structures described herein to together form an accessory that can be included with (i.e. sold together with) the stimulant target unit, or that could be sold separately from the stimulant target unit. Alternatively, any of the protective covers described herein could be sold as an accessory with, or separately from, the stimulant target unit, without being combined with any mounting structures.

It will be noted that the stimulant target units 100 are programmable to change their apparent size which can impact the apparent difficulty in hitting the target units 100 and as a result this can impact the amount of care that the player attempting to hit the target believes is required. Changing the apparent size of the target units 100 can be achieved by illuminating the LEDs 118 (FIG. 4) that are part of the inner annulus 114 (shrinking the apparent size of the target units 100), or illuminating the LEDs 122 that are part of the outer annulus 120 (expanding the apparent size of the target units 100).

Persons skilled in the art will appreciate that there are yet more alternative implementations and modifications possible, and that the above examples are only illustrations of one or more implementations. The scope, therefore, is only to be limited by the claims appended hereto.

What is claimed is:

1. A stimulant target unit, comprising:
 a housing;
 at least one stimulation source coupled to the housing, the stimulation source configured to provide a stimulus to stimulate a user;
 a contact sensor coupled to the housing and configured to detect an impact to the stimulant target unit;
 a feedback system configured to inform the user that the stimulant target unit has been actuated in response to the stimulus;
 a controller programmed to register triggering of the contact sensor;
 a protective cover configured to be positioned in front the housing and to transmit some impact force to the housing during some impacts; and
 a mounting structure configured to connect the stimulant target unit to a support structure, wherein the mounting structure includes a vibration isolator configured such that wherein, over a selected range of impact forces, the contact sensor is configured to be triggered by an impact that is within the selected range of impact forces, and wherein the vibration isolator inhibits transmission of force from an impact within the selected range of impact forces on the support structure to the contact sensor sufficiently to prevent the triggering of the contact sensor,
 wherein the housing includes a first shell connected to a second shell via an elastomeric rim,
 and wherein the rim has opposing first and second grooves and the first shell has a first axially extending flange along a periphery thereof,
 the second shell has a second axially extending flange along a periphery thereof, the first flange is disposed in said first groove and the second flange is disposed in the second groove, and the first flange ordinarily not bottoming in the first groove and the second flange ordinarily not bottoming in said second groove to thereby enable the first shell to move axially relative to the second shell upon impact.

2. A stimulant target unit according to claim 1, wherein the at least one stimulation source includes at least one of an auditory source to generate sound and a light source configured to generate light to be transmitted through the protective cover.

3. A stimulant target unit according to claim 2, wherein the light source includes a light emitting diode.

4. A stimulant target unit according to claim 1, wherein the vibration isolator includes at least one of a resilient member and a damping member.

5. A stimulant target unit according to claim 4, wherein the resilient member includes a spring.

6. A stimulant target unit according to claim 4, wherein the damping member includes a deformable member configured to absorb at least a portion of impact force on the support structure.

7. A stimulant target unit, comprising:
a housing;
at least one stimulation source coupled to the housing, the stimulation source configured to provide a stimulus to stimulate a user;
a contact sensor coupled to the housing and configured to detect an impact to the stimulant target unit;
a feedback system configured to inform the user that the stimulant target unit has been actuated in response to the stimulus;
a controller programmed to register triggering of the contact sensor, wherein the housing includes a primary contact member that is contactable to trigger the contact sensor over a first range of impact forces;
a protective cover positioned in front of the housing and spaced by a selected spacing from the primary contact member, wherein the spacing is selected to permit the protective cover to receive an impact and transmit the impact to the primary contact member to trigger the contact sensor over a second range of impact forces that is higher than the first range of impact forces, wherein the protective cover is removable so as expose the primary contact member of the stimulant target unit; and
a mounting structure configured to connect the stimulant target unit to a support structure.

8. A stimulant target unit according to claim 7, wherein the primary contact member is a first shell and wherein the housing includes a second shell to which the first shell is connected via an elastic member, such that the first shell is movable relative to the second shell upon impact on the protective cover in the second range of impact forces.

* * * * *